(12) United States Patent
Mullins et al.

(10) Patent No.: US 12,239,797 B2
(45) Date of Patent: Mar. 4, 2025

(54) CORRUGATED CATHETERS

(71) Applicant: Perfuze Limited, Galway (IE)

(72) Inventors: Liam Mullins, Galway (IE); Dara Finneran, County Roscommon (IE); Evin Donnelly, Galway (IE); Eoghan Thornton, County Galway (IE); Kieran Connolly, Galway (IE)

(73) Assignee: Perfuze Limited, Galway (IE)

( * ) Notice: Subject to any disclaimer, the term of this patent is extended or adjusted under 35 U.S.C. 154(b) by 621 days.

(21) Appl. No.: 17/620,028

(22) PCT Filed: Jun. 17, 2020

(86) PCT No.: PCT/EP2020/066829
§ 371 (c)(1),
(2) Date: Dec. 16, 2021

(87) PCT Pub. No.: WO2020/254447
PCT Pub. Date: Dec. 24, 2020

(65) Prior Publication Data
US 2022/0233814 A1    Jul. 28, 2022

(30) Foreign Application Priority Data

Jun. 18, 2019 (EP) .................................... 19180850

(51) Int. Cl.
*A61M 25/00* (2006.01)
(52) U.S. Cl.
CPC .... *A61M 25/0053* (2013.01); *A61M 25/0012* (2013.01); *A61M 25/0045* (2013.01);
(Continued)

(58) Field of Classification Search
CPC .......... A61M 25/0053; A61M 25/0012; A61M 25/0045; A61M 2025/0046; A61M 2025/006; A61M 25/0074
See application file for complete search history.

(56) References Cited

U.S. PATENT DOCUMENTS 5,938,587 A * 8/1999 Taylor .................... A61B 1/018
                                                      600/123
2005/0004560 A1 * 1/2005 Cox ....................... A61M 25/09
                                                      606/1

(Continued)

FOREIGN PATENT DOCUMENTS

EP           0861674 A1    9/1998
WO    WO 2018/011627      1/2018

OTHER PUBLICATIONS

International Search Report in PCT/EP2020/066829 dated Sep. 24, 2020, (5 pages).

*Primary Examiner* — Bradley J Osinski
(74) *Attorney, Agent, or Firm* — Bookoff McAndrews, PLLC

(57) ABSTRACT

A catheter (1) comprises a jacket (20, 33) and defining a lumen, and extends distally towards a tip (30, 31). The catheter has a helical support (20) within the jacket for at least some of the length of the jacket. The catheter distal end has a plurality of portions of different configurations for different bending and/or pushability characteristics. These may be according to different helical supports and the manner in which they are interwoven, and/or different liners with lap joints. There may be a hydrophilic coating.

15 Claims, 17 Drawing Sheets

(52) U.S. Cl.
CPC . *A61M 2025/0046* (2013.01); *A61M 25/0054* (2013.01); *A61M 2025/006* (2013.01)

(56) References Cited

U.S. PATENT DOCUMENTS

| | | |
|---|---|---|
| 2011/0288532 A1 | 11/2011 | Faherty |
| 2015/0174364 A1 | 6/2015 | Kennelly |
| 2018/0015248 A1 | 1/2018 | Logan |
| 2018/0015254 A1 | 1/2018 | Cragg |
| 2020/0206458 A1 | 7/2020 | Mullins |
| 2021/0361910 A1 | 11/2021 | Mullins |

* cited by examiner

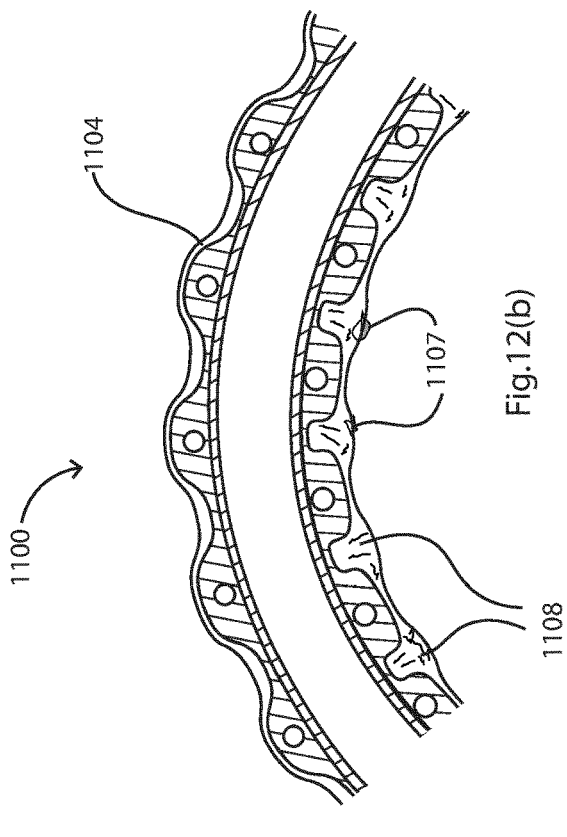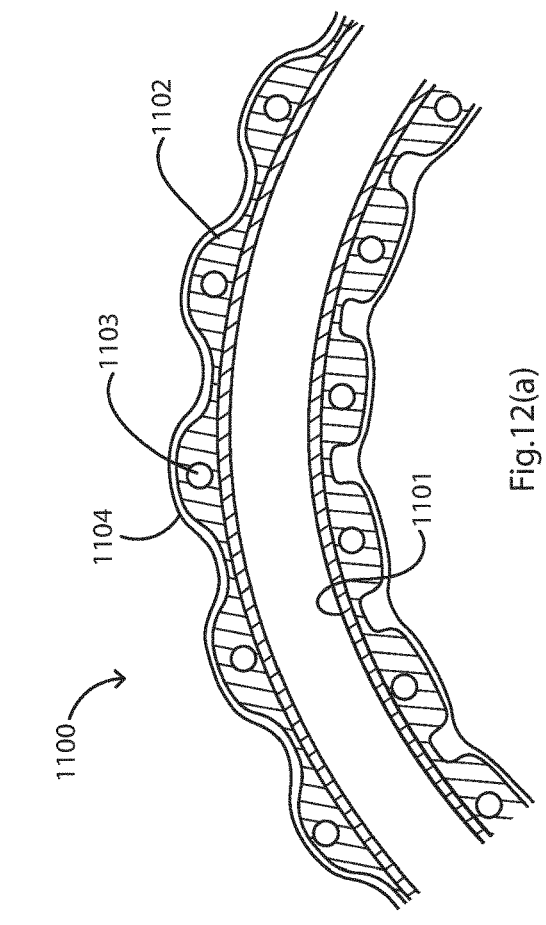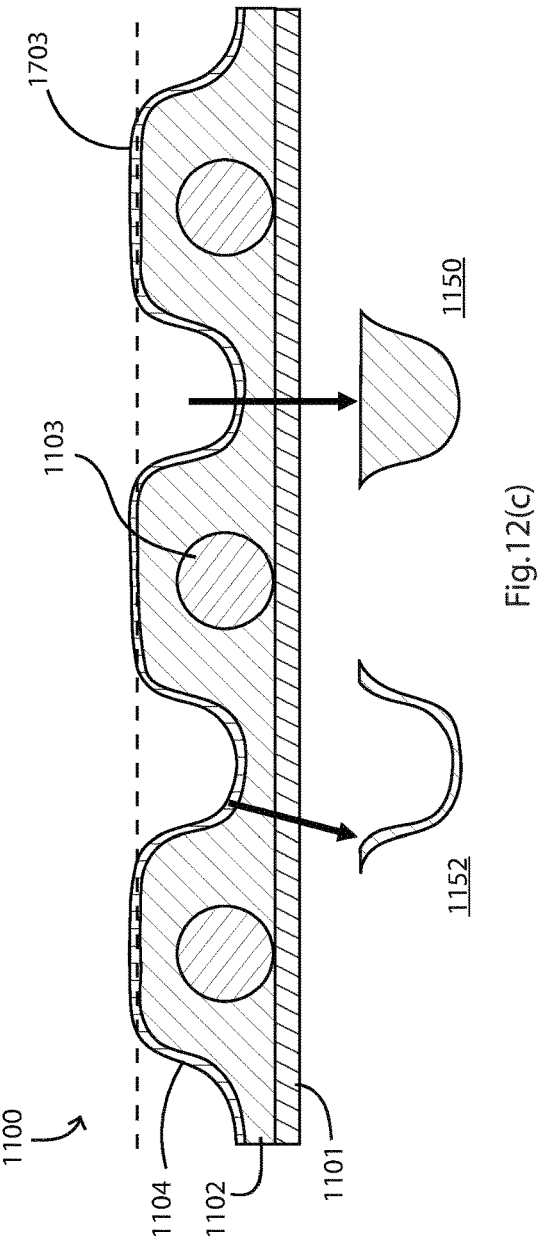

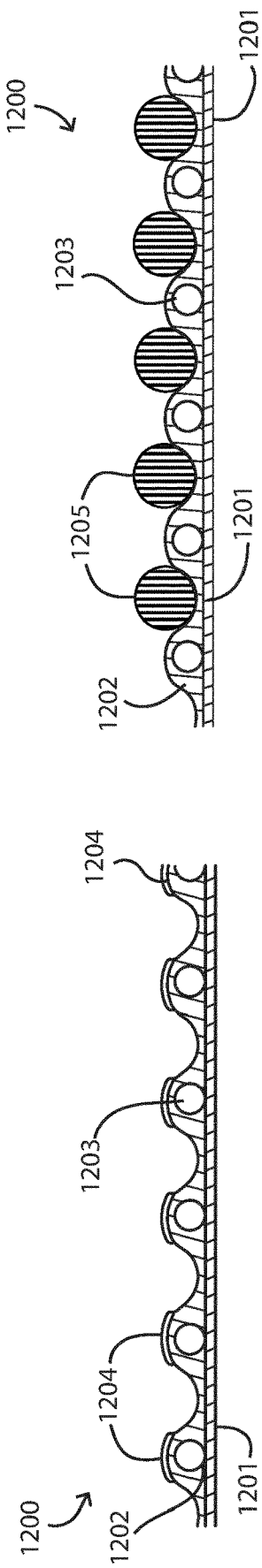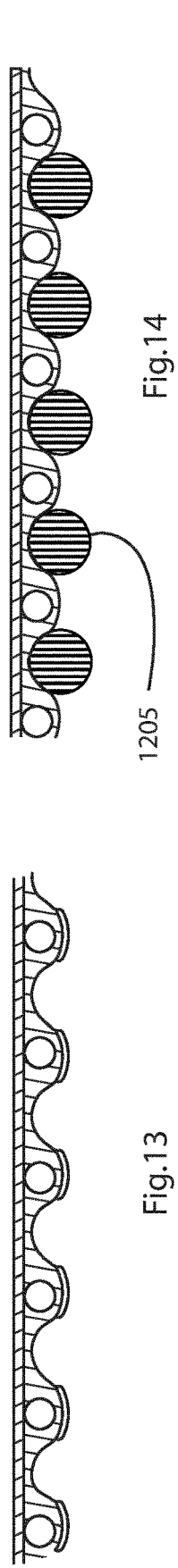
Fig.14
Fig.13

CORRUGATED CATHETERS

CROSS-REFERENCE TO RELATED APPLICATIONS

This application is the U.S. national phase entry under 35 U.S.C. § 371 of International Application No. PCT/EP2020/066829, filed on Jun. 17, 2020, which claims benefit to European Patent Application No. 19180850.0, filed on Jun. 18, 2019, the contents of which are incorporated herein by reference in their entireties.

INTRODUCTION

The invention relates to catheters with flexibility and kink resistance, for medical applications such as endovascular procedures.

WO2018/011627 (Neuvt Limited) describes various catheters of this type.

The invention is directed towards providing improvements to catheters and their manufacture and use.

SUMMARY

We describe catheters as set out herein, catheter assemblies as set out herein, methods of use of an assembly as set out herein, and methods of manufacture of a catheter as set out herein.

We describe a catheter comprising a jacket and defining a lumen, and extending distally towards a tip, the catheter comprising a helical support within the jacket for at least some of the length of the jacket, wherein the catheter distal end has a plurality of portions of different configurations for different bending and/or pushability characteristics.

Preferably, a distal-most portion does not include a helical support.

Preferably, a distal-most portion has one or more radiopaque bands. Preferably, a more proximal portion has corrugations which have a smaller depth and/or width. Preferably, a more proximal portion is un-corrugated. Preferably, a more proximal portion has a jacket material of a greater stiffness than a next distal-most portion. Preferably, the jacket includes urethane.

Preferably, a more distal portion comprises jacket material including urethane of about 70A to 90A durometer, more preferably about 80A durometer. Preferably, a more distal portion has a floating unbounded helical support.

Preferably, a more distal portion comprises inner and outer layers of material such as ePTFE with a helical support unbonded within a helical channel. Preferably, the helical support has a varying pitch in the longitudinal direction. Preferably, the helical support pitch increases distally for at least some of the length of the catheter.

Preferably, the helical support pitch increases distally for at least some of the length of the catheter, and there are increases and decreases in stiffness.

Preferably, a more proximal portion has a jacket which bonds to the helical support, the helical support being constrained from movement relative to the surrounding jacket material, and the jacket material which bonds to the helical support may include urethane.

Preferably, adjoining portions have jackets of differing stiffness, more flexible distally. Preferably, an increased hardness jacket is provided next to a lower hardness jacket, and an increase in the degree of corrugation locally is provided to avoid a sudden increase in stiffness.

Preferably, there is a reducing jacket thickness in a more distal portion in order to increase flexibility distally.

Preferably, the lumen is provided by a liner. Preferably, the lumen is provided by a liner having different materials joined at a joint. Preferably, the joint is in a portion with an un-corrugated jacket.

The lumen may be provided by a liner having different materials joined at a joint, and the liner material transitions from ePTFE to PTFE.

The lumen may be provided by a liner having different materials joined at a joint, and the transition or switch is in an area of jacket of higher stiffness or durometer than a most distal portion. Preferably, the lumen is provided by a liner having different materials joined at a joint, and the liner joint or transition is preferably at least 5 cm from the catheter tip.

The lumen may be provided by a liner having different materials joined at a joint, and the liner joint spans portions with jackets of different hardness, a distal portion jacket having greater flexibility. Preferably, the lumen is provided by a liner which does not extend to the tip. Preferably, the helical support has a longer pitch closer to the distal end. Preferably, the helical support does not extend to the tip.

Preferably, the catheter has a hydrophilic coating over at least one portion. Preferably, the catheter has a hydrophilic coating over at least one portion, and wherein the coating is applied across at least 20 cm of the catheter length.

The catheter may have a hydrophilic coating over at least one portion and the coating has a primer layer of material such as urethane.

Preferably, the catheter has a hydrophilic coating over at least one portion, and the coating layer or layers are less than 0.002 in in thickness, and preferably the coating thickness is less than 0.001 in in thickness.

Preferably, the catheter has a hydrophilic coating over at least one portion, and the coating comprises a hydrogel which fills at least part of the corrugate.

Preferably, the catheter has a hydrophilic coating over at least one portion, and the coating comprises a hydrogel which fills at least part of the corrugate, and hydrogel material has a stiffness lower than that of the (e.g. urethane) jacket material, and preferably said filling enables a smooth outer surface, or cushion, for contact with a vessel wall, while the hydrogel provides lubricity without increasing the stiffness of the catheter section significantly.

Preferably, the tip of the catheter is expandable to enable it to accept a clot or embolus when a vacuum is applied. The tip may include a radial support such as a stent-like structure which can deform radially to enlarge and engulf the embolus.

Preferably, the tip diameter tapers towards the end, but is expandable upon the application of a vacuum and entrance of an embolus into the catheter tip.

The catheter may comprise a radial support within the jacket at or adjacent the distal tip, and preferably said support comprises a ring which is not continuous and has a cut. Preferably, the cut is configured so that the radial support can open to allow the distal tip diameter to increase, but cannot reduce in diameter, preserving the lumen of the catheter during vacuum.

We also describe methods of manufacture of a catheter as described in any example. The method may include steps of placing a liner of material such as ePTFE on a mandrel, placing a helical support on the liner, and dip coating to apply a corrugated jacket, in which the coating takes the geometry of the liner and the helical support. There may be further dip coating steps to build up the jacket thickness such that the corrugations remain true and do not fill.

Preferably, the method including steps of stretching a liner in order to alter the directionality of the liner material (e.g. ePTFE) fibres and reduce the wall thickness as required. The liner may be radially stretched, preferably by at least 10% in diameter.

The method may include setting force required to bend the catheter by linear pre-stretching or shortening of the liner and/or jacket material.

The method may include etching to improve the potential to bond the jacket to the liner, and/or to induce shortening, and/or working or pre-conditioning the jacket and the liner using a series of bend and/or tension and/or compression cycles to enhance flexibility.

DETAILED DESCRIPTION OF THE INVENTION

The invention will be more clearly understood from the following description of some embodiments thereof, given by way of example only with reference to the accompanying drawings in which.

Figure 10:
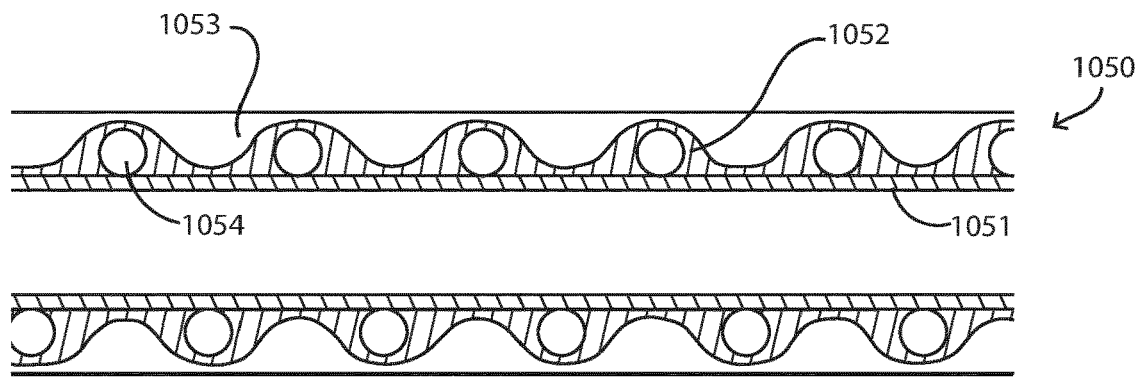
Figure 11:
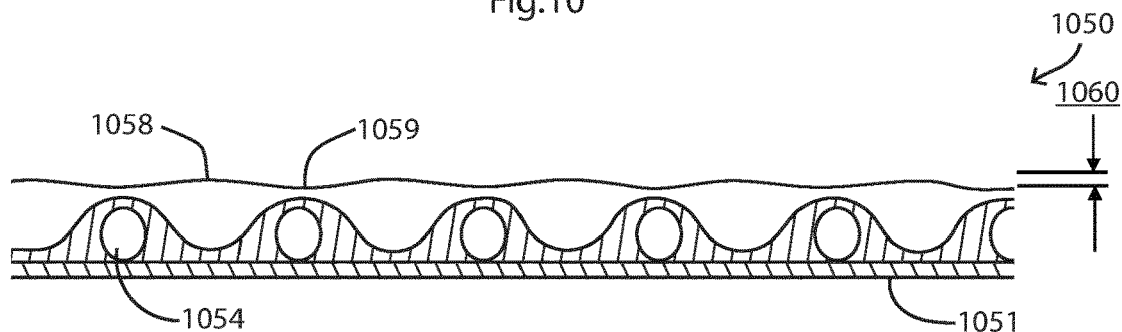
Figure 15:
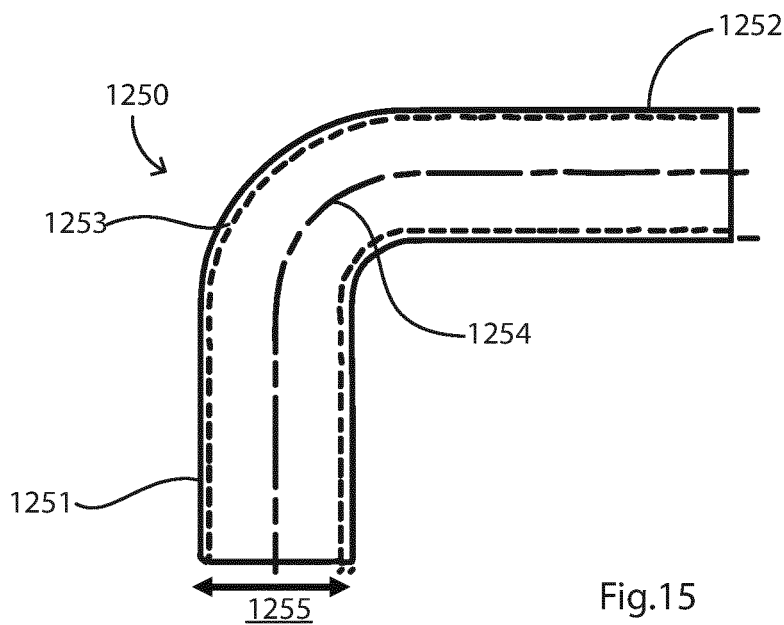
Figure 16:
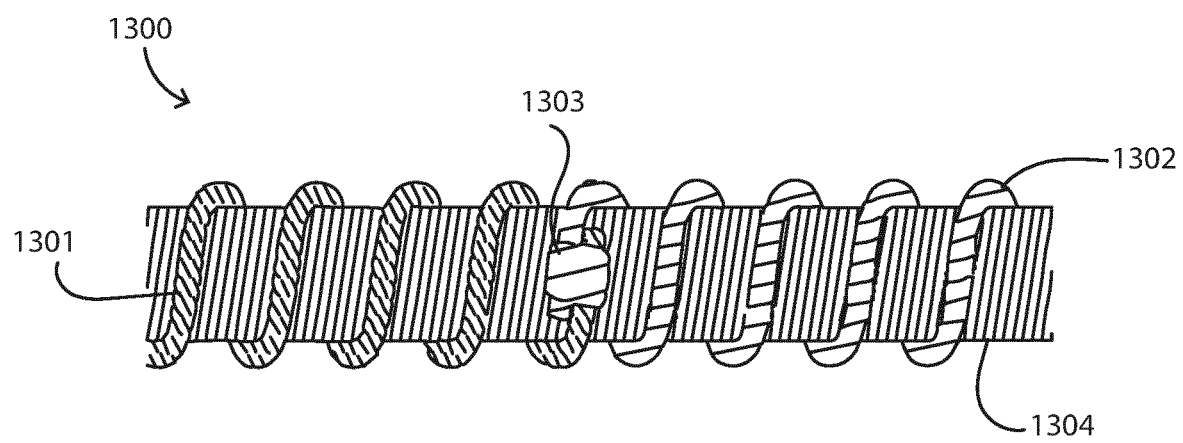
Figure 17:
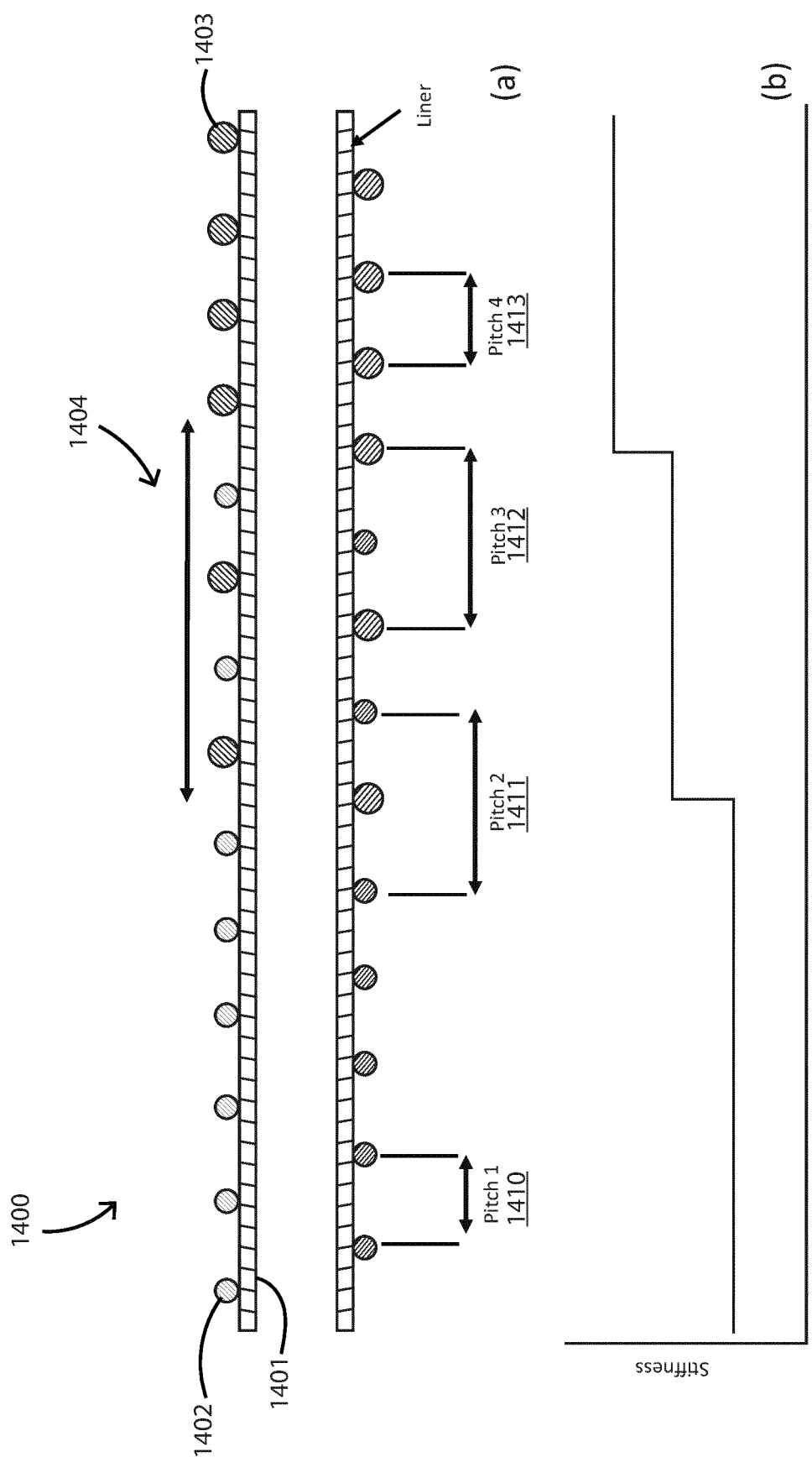
Figure 18:
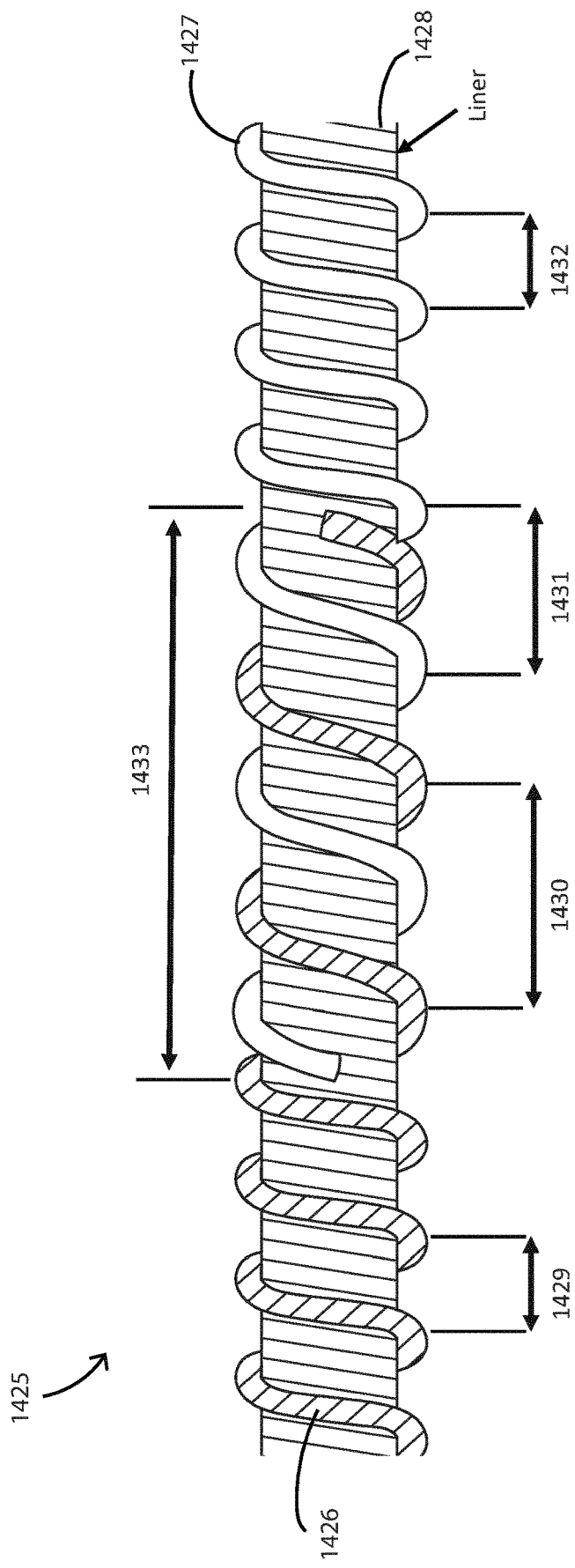
Figure 19:
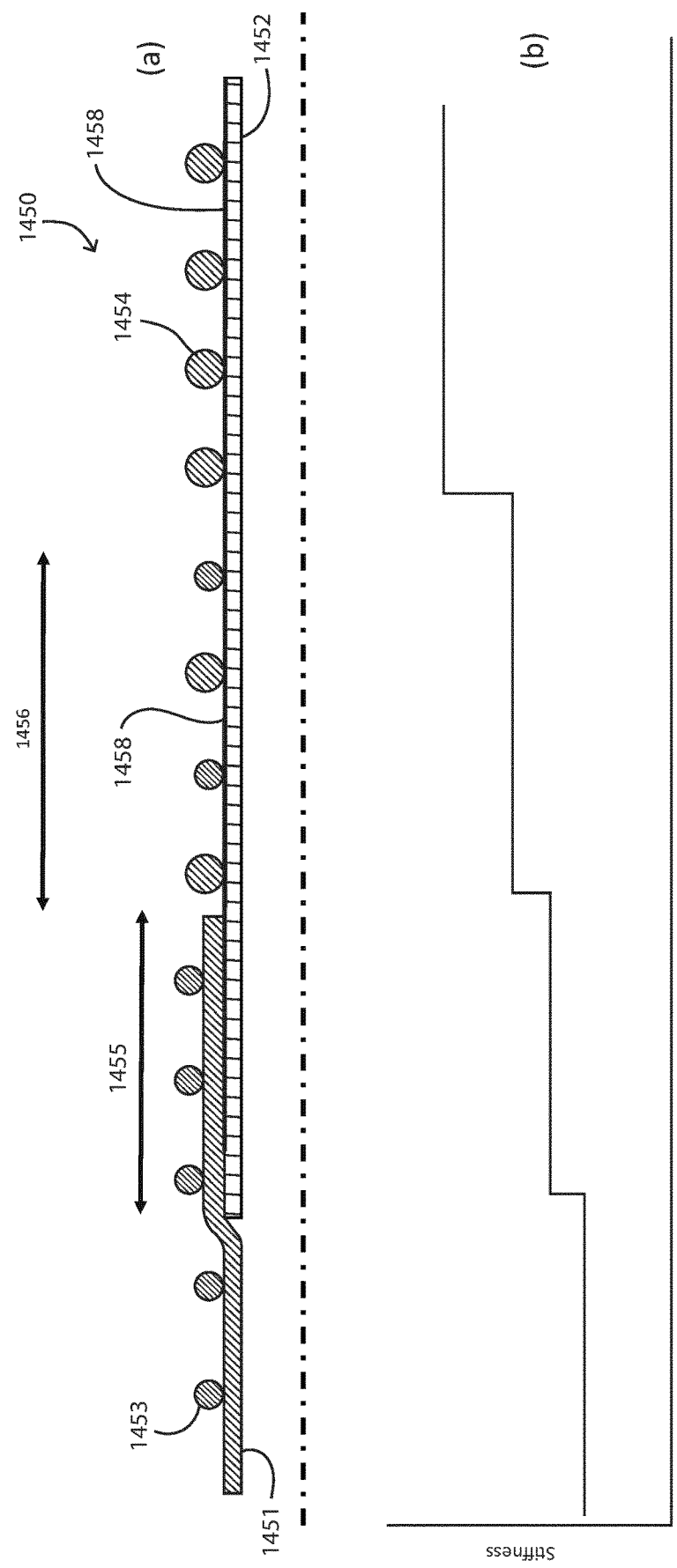
Figure 20:
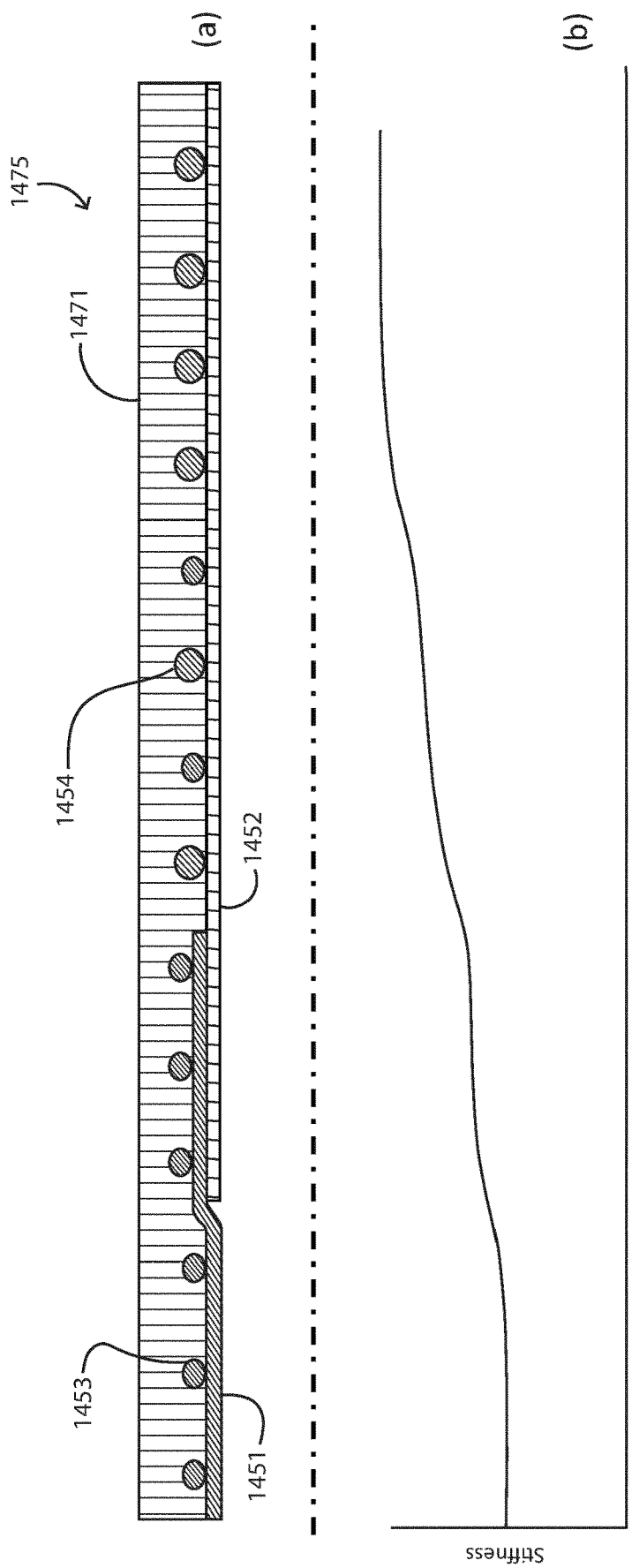
Figure 21:
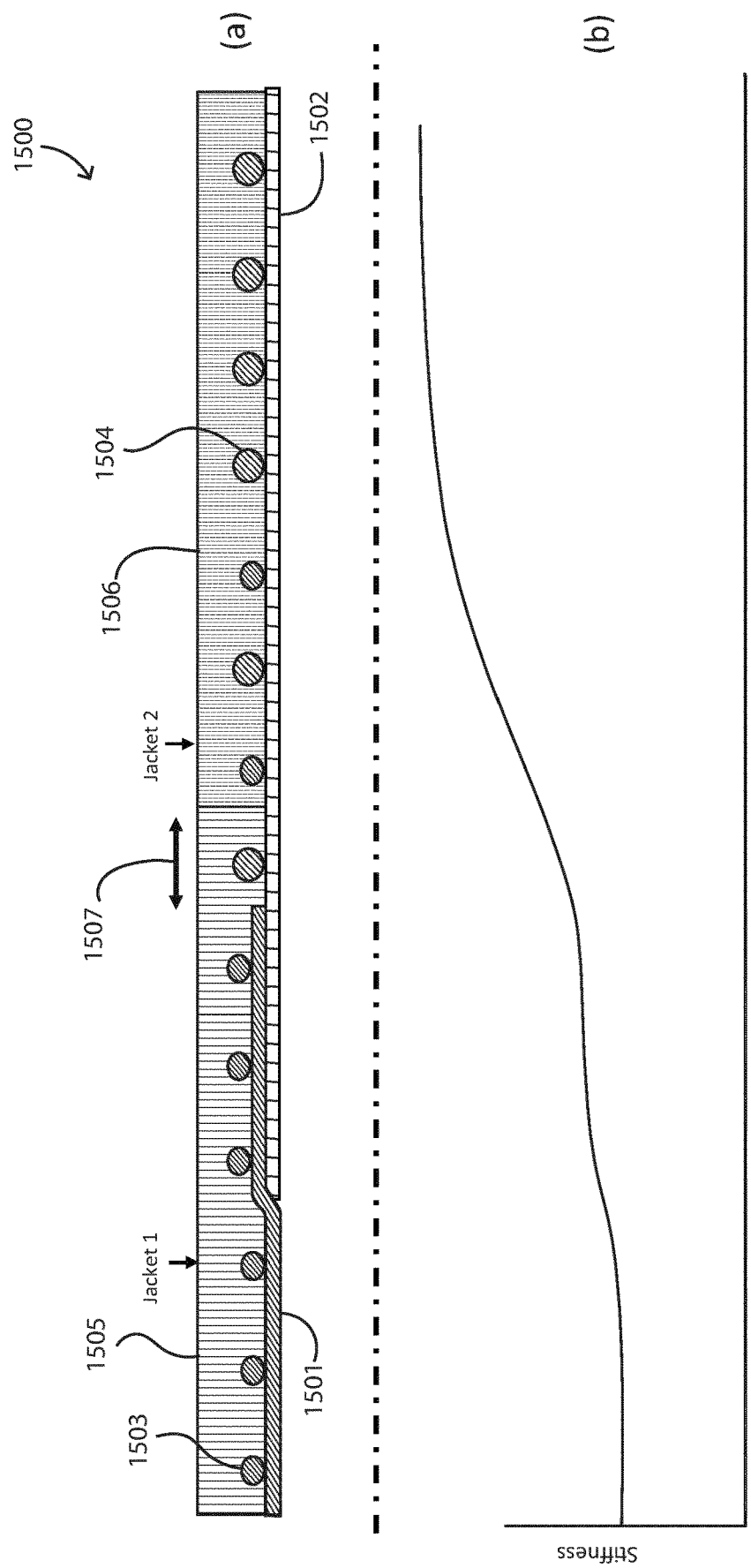
Figure 22:
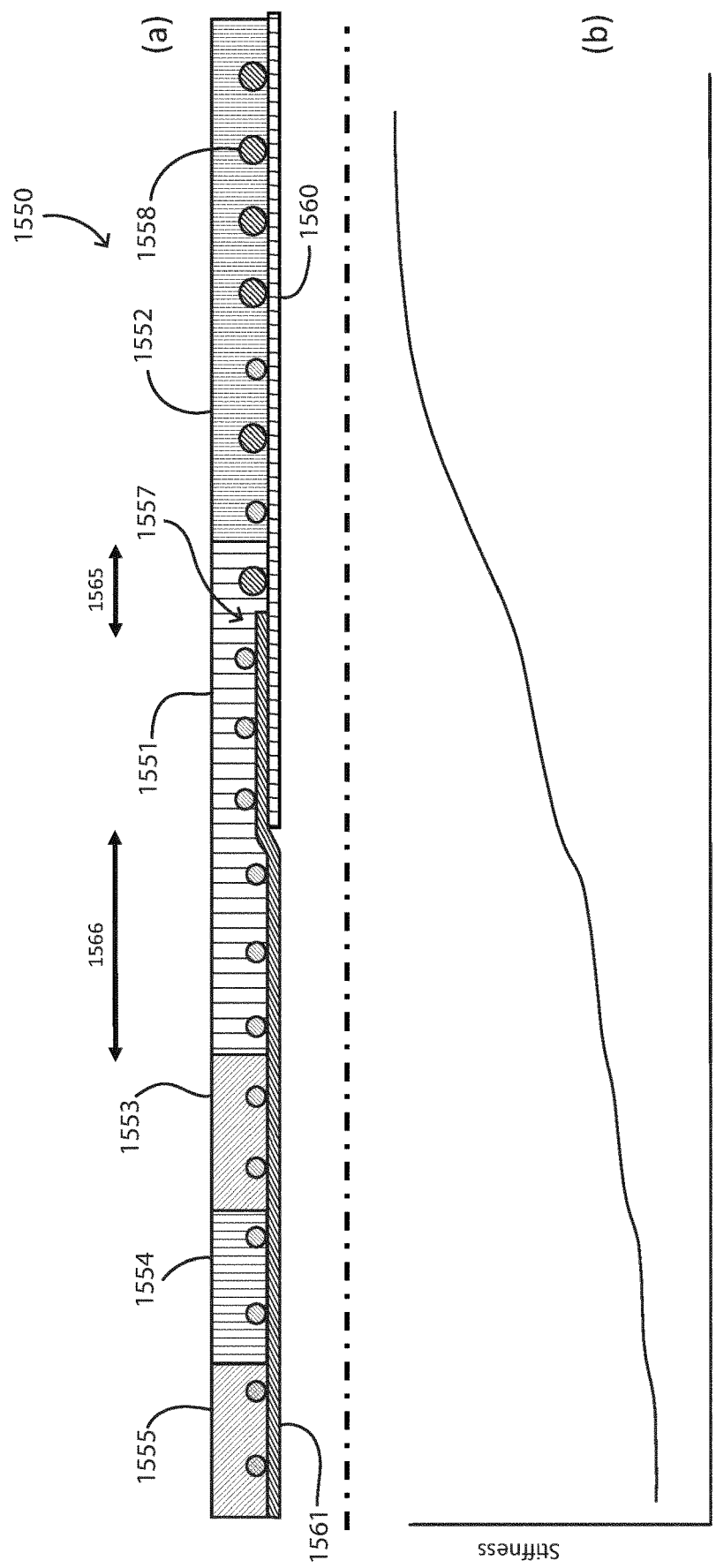
Figure 23:
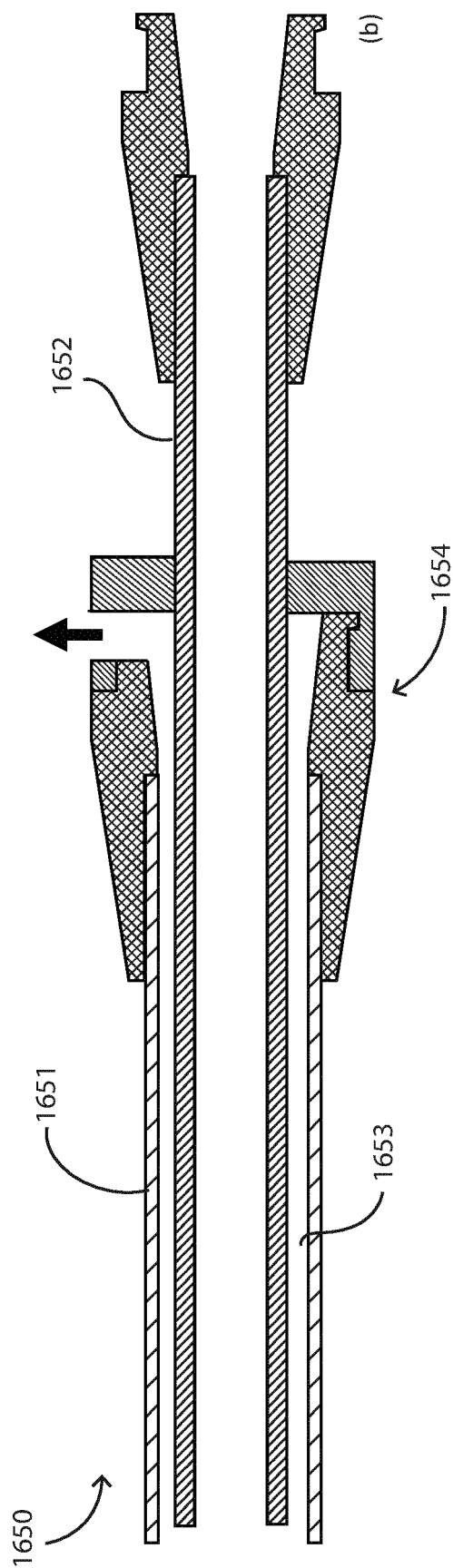
Figure 24:
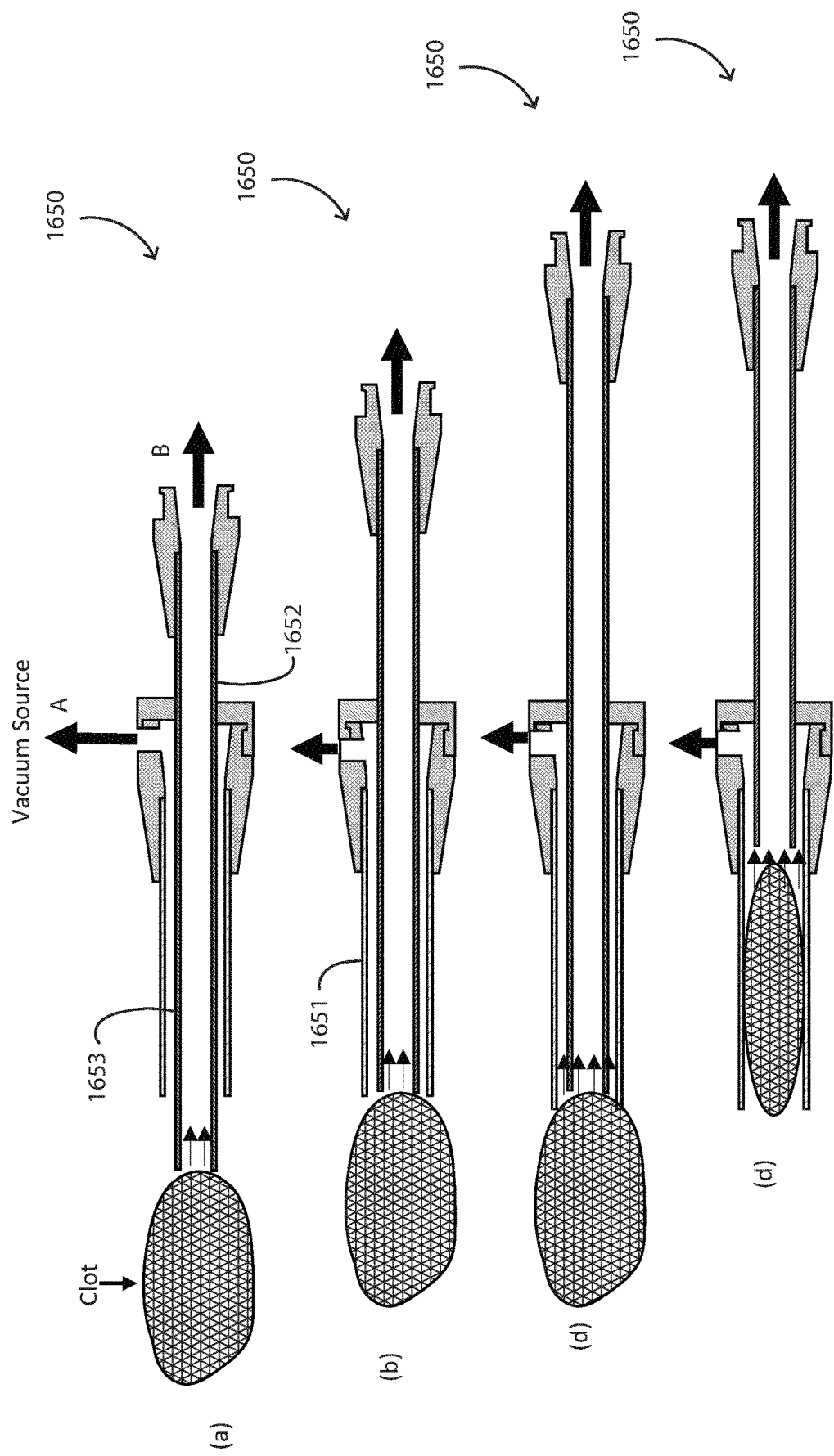
Figure 25:
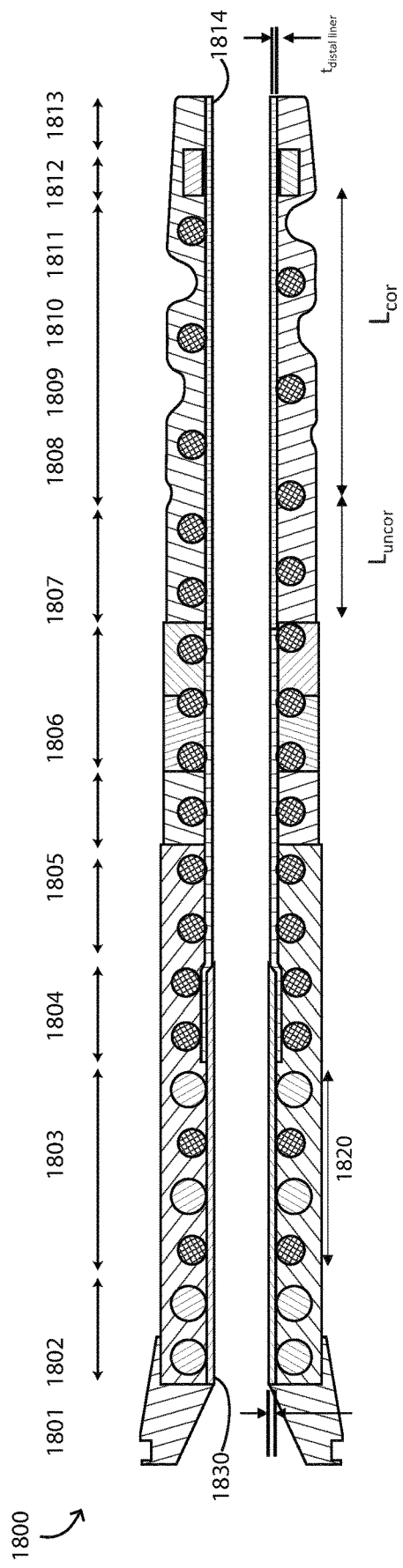

FIGS. 9(*a*) and (*b*) are diagrams showing part of the length of a catheter with a hydrophilic coating, showing the difference between dry and hydrated states;

FIG. 10 shows a catheter with a deep hydrophilic coating;

FIG. 11 shows how a mild corrugated surface may develop in the surface of a hydrophilic coating, in the opposite sense to the underlying jacket material corrugation;

FIGS. 12(*a*) and 12(*b*) show shape effects during bending of a catheter, and possible delamination on the concave side, and 12(*c*) shows the relative volumes of the recess and the hydrophilic coating within the recess respectively, of a corrugate;

FIGS. 13 and 14 show part of a catheter with selective hydrophilic coatings on corrugation ribs, and a manner of application of such coatings;

FIG. 15 shows bend parameters;

FIG. 16 shows a catheter having a transition from one helical support to another, with a connector element;

FIG. 17 shows a catheter having different and interwoven helical supports with different pitches to achieve reduced steps in stiffness in the longitudinal direction;

FIG. 18 shows an alternative arrangement with interwoven helical supports;

FIG. 19 shows a still further arrangement, in this case with a liner lap joint and interwoven helical supports;

FIG. 20 shows a catheter with a liner lap joint and a constant diameter jacket without corrugations in this region of the catheter;

FIG. 21 shows an arrangement in which there are transitions from one type of jacket material to another near the location of a lap joint between liners, and helical supports being interwoven across the jacket material joint and the lap joint, and FIG. 22 shows an alternative with more transitions between jacket materials, and again this region of the catheter does not have corrugations;

FIG. 23 shows part of an assembly of a mother and daughter catheter and vacuum fixtures, and FIG. 24 shows stages of clot retrieval with such an assembly; and FIG. 25 is a diagram showing transitions between catheter portions in a direction from proximal (left) and distal (right) in one example having some of the features illustrated in the other drawings.

DETAILED DESCRIPTION OF THE EMBODIMENTS

Figure 1:
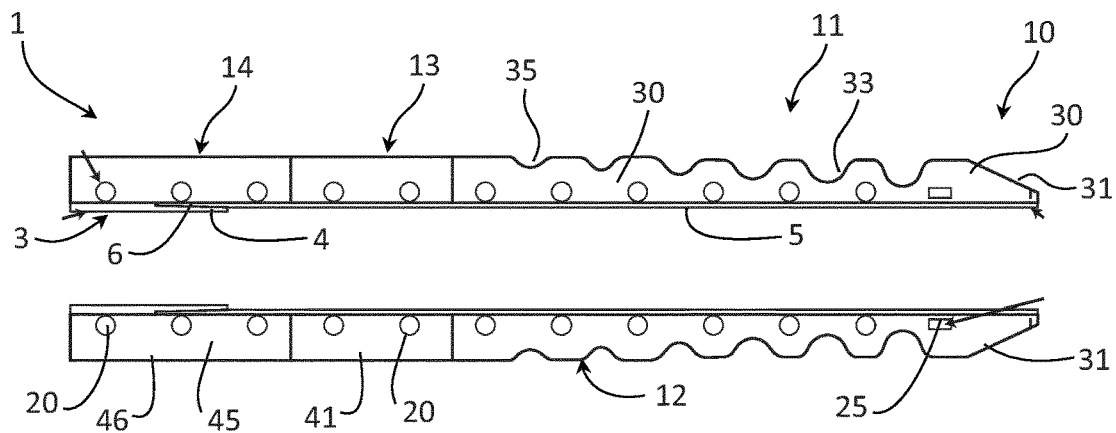
FIG. 1 is a sectional side view of distal portions of a catheter.

Referring to FIG. 1 this shows the distal portions of a catheter 1 including the following from a tip (distal end) proximally:

A first portion 10 forming a tip of jacket material 30 with a tapered profile narrowing in the distal direction, and embedding a radiopaque ring 25.

A second portion 11 with the jacket material 30 encapsulating a helical support 20 (which extends further proximally), and having corrugations 33.

A third portion 12 with the jacket material 30 encapsulating the helical support 20, and having shallower corrugations 35. The corrugations 35 have in this case the same Pitch as the more distal corrugations 33, but the depth door of the recesses is smaller.

A fourth portion 13 of different jacket material 40 encapsulating the helical support 20 and having a non-corrugated cylindrical outer surface.

A fifth portion 14 of different jacket material 45 and having a non-corrugated cylindrical outer surface 46.

The portions 10, 11, 12, and 13 include a liner tube 5 which defines the lumen, and the portion 14 includes a liner tube 3 and a joint 6. The jacket materials 30, 41, and 45 are different in terms of flexibility being more flexible towards the distal end.

Figure 2:
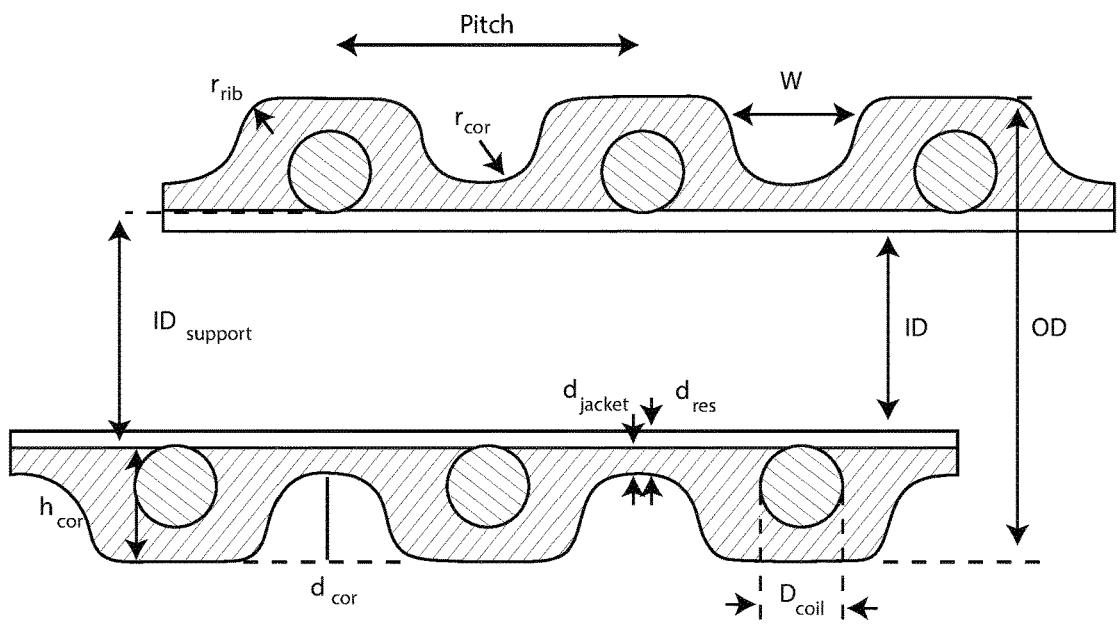
FIG. 2 is a schematic illustrating dimensions on a cross section of a corrugate geometry of catheters, showing depth of corrugate ($d_{cor}$), radius of fillet of corrugate rib ($r_{Rib}$), radius of the inside of the corrugate ($r_{Cor}$), height of the corrugate ($h_{Cor}$), length (or "wavelength") of a corrugation unit ($l_{cor}$), and residual depth ($d_{res}$)

For various catheters described here some dimensions defining corrugations are illustrated in FIG. 2:

Pitch is the peak-to-peak longitudinal distance, the wavelength;

W is the width (in the longitudinal direction) of a trough of a corrugation;

$d_{cor}$ is the depth of a corrugation trough (or height of a corrugation rib);

$r_{rib}$ is the radius of curvature of a corrugation rib;

$r_{cor}$ is the radius of curvature of a corrugation trough;

$d_{res}$ is the height (radial dimension) of the jacket at the bottom of the trough; and $h_{cor}$ is the height (radial dimension) of the corrugation Referring again to the catheter 1 of FIG. 1, it has a flexible tip which is more flexible distally than proximally. In the distal portions 10, 11, and 12 the jacket material 30 is urethane bonded to the liner 5 comprising:

Compressible material or fibrous material.

Preferably ePTFE: Density, thickness per tables below.

The more distal portions of the ePTFE lined distal jacket are corrugated and the fourth and fifth portions are un-corrugated.

In this example the corrugations are more pronounced, deeper and and/or wider, in at least one more distal portion than in at least one more proximal portion. The recesses are deeper distally than proximally, meaning the residual material beneath the recess is lower distally than proximally. In another embodiment the recesses are constant in depth and width, but the residual material beneath is lower distally than proximally. Once the width of a recess reaches a certain value it may remain constant even as the depth of the recess, and or depth of the residual material beneath the recess is lower distally than proximally.

The corrugations represent the impression of a circular wire applied around the outer jacket surface during manufacture. The diameter of the wire is according to the table below in various examples. The corrugations are wide enough to allow a lower bend radius distally than proximally, and are deep enough to allow a lower bend radius distally than proximally without contact between adjacent corrugates (or ribs).

The volume of jacket (e.g. urethane) material per unit length of catheter length can vary:
  Being lower distally than proximally, to enhance flexibility.
  Being lower distally than proximally such that the height of the rib of the corrugate is controlled so that the outer diameter of the catheter does not increase from at least one portion to the next in the distal direction.
  Corrugation geometry is such that the radius of bending at which adjacent corrugations come into contact is lower in the distally than proximally. This may be achieved by controlling the height and width of the corrugation.

These attributes are achieved by the physical parameters, especially width, of the corrugation as set out in the tables below, the parameters of which are illustrated in FIG. 2. The top surface of the rib is preferably curved. The area between the convex curve of the rib and concave curve of the recess is preferably curved or filleted such that it does not represent a square edge. A square edge is to be avoided as it will cause adjacent corrugations to come into contact at a lower bend radius. A fillet, with a radius $r_{rib}$ is preferable as shown in FIG. 2.

In a more proximal portion, the liner material transitions from ePTFE to PTFE. The transition or switch is in an area of jacket of higher stiffness or durometer than the most distal portion.

The more distal portion jacket material is preferably in some examples a urethane of about 70A to 90A durometer, more preferably 80A durometer.

The liner transition is preferably at least 5 cm from the catheter tip.

The most distal portions (length between 0.5 mm to 2 mm) are preferably more flexible, achieved for example by:
  Being corrugated and without any helical support, and/or
  Being un-corrugated and without any helical support, and/or
  Having a radiopaque marker proximal of a more flexible distal portion.

Potential dimensions are outlined for an 8F configuration of the catheter with ID in the order of 2.24 mm (0.088 in).

TABLE 1

| Attribute | Range | Preferably |
|---|---|---|
| Catheter Outer Diameter (mm) | 2.3-2.7 | 2.64 |
| Catheter Inner Diameter (mm) | 1.7-2.4 | 2.24 ± 0.1 |
| Distal Corrugation Depth (mm) | >0.025 | >0.19, more ideally ≥0.24 |
| Distal Residual Depth (mm) | <0.2 | <0.1 |
| Distal Corrugation Width (mm) | >0.05-0.51 | 0.10-0.31 |
| Distal combined thickness of liner and residual jacket (mm) | <0.15 | <0.10 |
| Recess Geometry | Round, U, V, Square | U |
| Rib Geometry | Avoid square profile | Rounded edge, or inverted U |
| Rib fillet radius ($r_{rib}$) (mm) | >0.025 | |
| Length of Corrugated Section (cm) | >2 | >6 |
| Length of Uncorrugated Section of Distal Jacket (cm) | >1 | >4 |
| Liner Material | Fibrous or compressible | ePTFE |
| Liner Density (g/cm³) | 0.4-1.2 | <0.8 |
| Liner Thickness pre-assembly (mm) | 0.025-0.102 | <0.076 |
| Liner Strike Layer | None or TPU or Polyamide | Polyamide 35D |
| Liner Condition on Mandrel Distal Section of Tip | Radially Stretched | Radially stretched, Axially Compressed |
| Liner Condition on Mandrel Proximal Section of Tip | Radially Stretched | Radially Stretched |
| Uncoiled section 80A length (mm) | 0.5-2 | 0.5-1 |
| Helical Support Diameter (mm) | 0.076-0.127 | 0.102 |
| Location of Corrugated Section | Within 80A section | Within 80A section |
| Location of ePTFE and PTFE Joint | Proximal to corrugated 80A section | Proximal to 80A Section, or within 40D Section |
| Distance of ePTFE and PTFE Joint within 40D, from 80A (cm) | >0.5 | >1 |
| Type of Joint of ePTFE and PTFE | Overlap or Butt | Overlap |
| Corrugation Pitch (mm) | 0.13-0.076 | 0.38-0.63 |
| Corrugated Section Length (cm) | >2 | >6 |
| Variance in depth, width of corrugation | Variable along length (increasing distally) | |
| Cinch Wire Diamete (mm) | 0.2-0.040 | |
| Winding Tension Applied to Cinch Wire at Proximal End (N) | >0.5 | >0.5 |
| Force Applied at Distal End (N) | >7 | >10 |
| Distal Jacket Material | TPU or Pebax | 80A TPU |
| Proximal Jacket 1 ID Pre Lamination (mm) | >2.5 | |
| Proximal Jacket 1 Thickness Pre Lamination (mm) | >0.102 | 0.15-0.20 |
| Distal Jacket ID Pre Lamination (mm) | >2.5 | |
| Distal Jacket thickness Pre-Lamination (mm) | 0.076-0.175 | <0.127 |
| ePTFE Liner Inner Diameter Stretching for Pre-Placement on Mandrel (mm) | 0.76-2.4 | 1.3-1.8 |
| ePTFE Liner Inner Diameter Post Stretching for Pre-Placement on Mandrel (mm) | 1.7-2.4 | 2.24 ± 0.1 |
| ePTFE Liner Condition on Mandrel Proximal | Radially Stretched | Radially and Longitudinally Stretched |

TABLE 1-continued

| Attribute | Range | Preferably |
|---|---|---|
| Cinch Wire Shape | Round, Square, or Angled | Round |
| Length of Overlap (cm) | 1-3 | 1 |

Table 1—Example dimensions. Dimensions are indicative of an 8F OD, 0.088 ID catheter. They may be scaled up or down depending on the required ID (internal diameter) and (external diameter) OD of the catheter i.e. the same or similar ratios of dimensions may be applied for larger or smaller ID and OD catheters.

Corrugation Geometries During Bending

Figure 3:
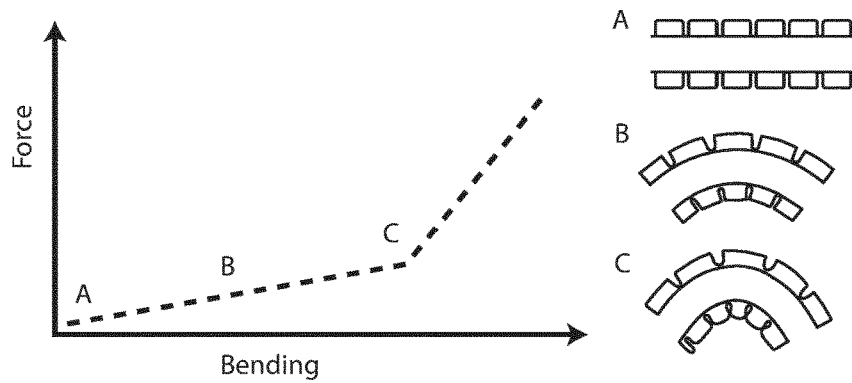
FIG. 3 is a schematic demonstrating how as a corrugated catheter geometry is bent, in which adjacent corrugations come into contact, increasing force is required to continue to bend the catheter.

Consider a corrugated catheter in bending as shown in FIG. 3. For lower degrees of bending A-B adjacent corrugations will not be in contact. During this phase of bending the force required is relatively low. Eventually as further bending is applied the corrugations will come into contact (C), or bottom out. At this point the force required to bend the catheter will increase substantially. In order to maintain a low force during bending it is advantageous to ensure adjacent corrugations do not come into contact for the largest degree of bending deformation possible (i.e. the lowest bend radius). This will allow the catheter to navigate the vasculature at low force, without the potential for vessel damage or perforation. It also decreases the amount of energy required to push the catheter along an area.

Figure 4:
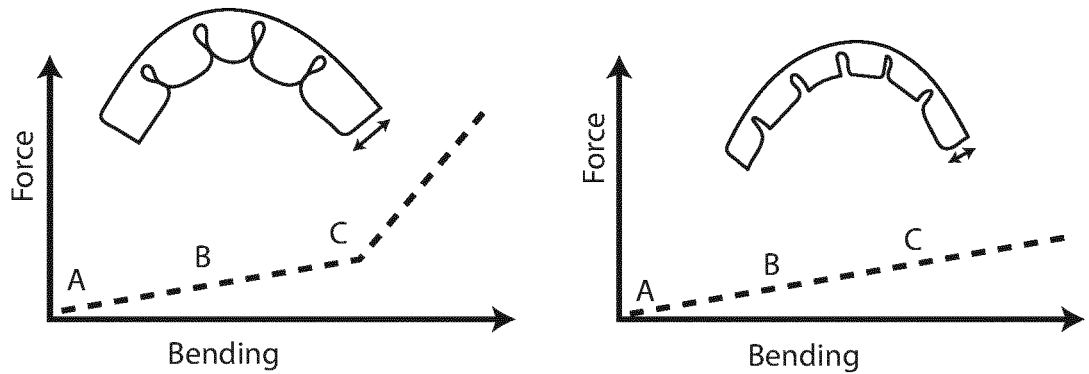
FIG. 4 is a schematic demonstrating how a larger corrugate depth and height means corrugations will come into contact during bending, increasing the force and energy required to bend the section of corrugated catheter.

Contact between adjacent corrugations may be avoided by reducing their height ($h_{cor}$) and depth ($d_{cor}$) as shown in FIG. 4. The desired dimensions will depend on the degree of flexibility and radii of curvature of the target anatomy in which the catheter will be used. Preferable dimensions are outlined in Table 1 above. Referring to the letters A, B, and C, in FIG. 4 the plots The plots show two corrugation geometries; the first in which the adjacent corrugations have come into contact, and a second where the width of the corrugations has been increased to prevent corrugations coming into contact at the equivalent amount of bending, thus allowing increased bending to take place at a lower Force.

In one embodiment a round edge, or fillet, is present on the rib to avoid a square edge ($r_{rib}$). This will mitigate contact between adjacent corrugates. A larger fillet will enable adjacent corrugations to come into contact a lower bend radius. Preferable dimensions are outlined in Table 1.

In another embodiment, the rib shape is more akin to an inverted V shape or saw-tooth. This significantly mitigates contact between adjacent corrugates. The angle of the inverted V should be greater than 10° to achieve this effect.

Width of the corrugate is also important, because in the absence of a corrugation width (W), or relatively wide recess, the catheter may not achieve significant flexibility, and low forces of bending. Preferable dimensions are outlined in Table 1. Increasing corrugate width also has the effect of mitigating contact between corrugates.

Polymers used in catheter manufacture are, in the main, incompressible materials. This means that, as they are deformed the volume of material remains substantially constant. In one process of manufacture the outer layer of material is corrugated using a cinch wire. The cinch wire is under tension such that an impression is made on the outer layer. As the tension is increased the cinch wire will displace material under the wire thereby creating a recess and forcing the material into a less constrained region, creating a rib. This rib and recess configuration enables improved flexibility since residual depth ($d_r$) is reduced, FIG. 2. Heating may be used to permanently set the rib and recess configuration prior to removal of the cinch wire.

While increased tension on the cinch wire will deepen the impression of the corrugation resulting in a lower residual depth ($d_r$), it will also increase the height of the corrugation ($h_{cor}$) such that the outer diameter of the catheter increases in that region. Furthermore, it will increase the width of the corrugation to limit approaching the diameter of the cinch wire. It should be noted that following heat setting and removal of the cinch wire some relaxation of the polymer occurs, typically leaving maximum corrugate width which is less than that of the diameter of the cinch wire, usually of the order of 50% to 95% of the cinch wire. For 80A pellethane this is of the order of 75% of the diameter of the cinch wire. This geometry is shown schematically in FIG. 5 and FIG. 2.

Figure 5:
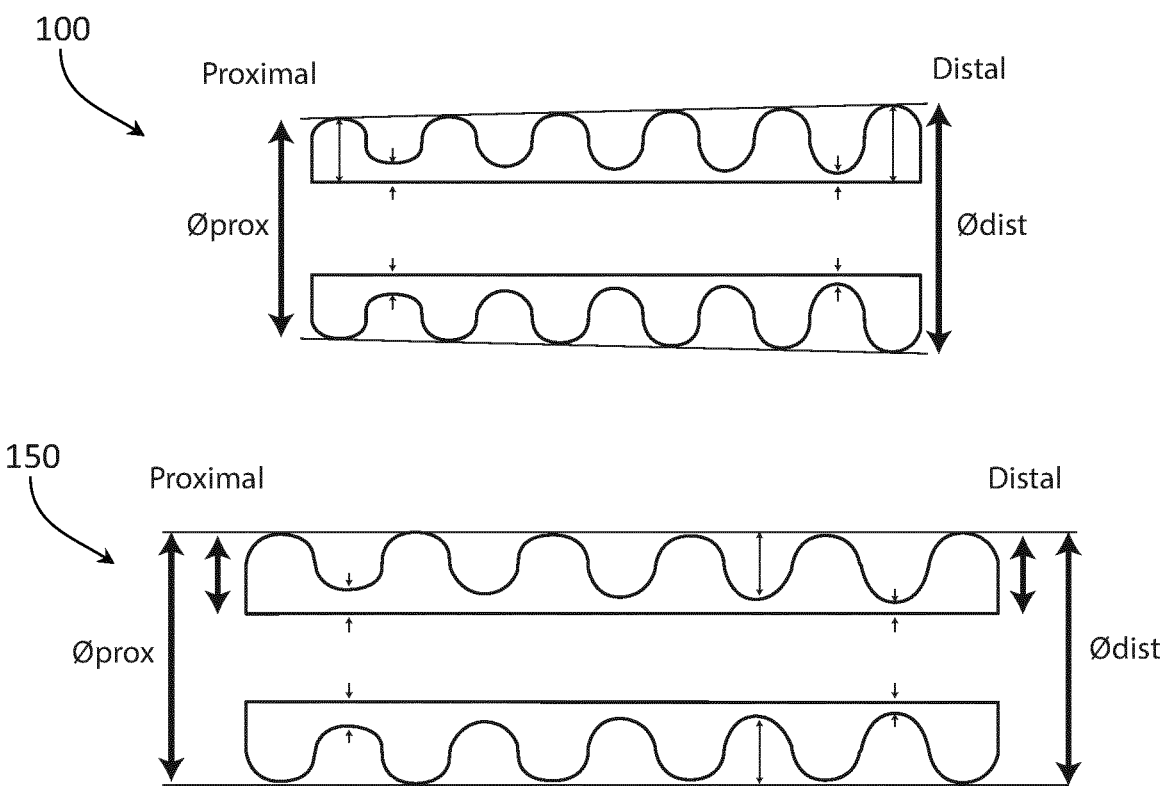
FIG. 5 is a sectional view showing a portion of a catheter in which there is a more gradual increase in depth of corrugations in the longitudinal direction.

This will increase the outer profile of the catheter meaning it requires a larger arteriotomy (hole) for insertion. The residual depth shown in FIG. 5 is the combined depth of the liner and jacket. While the corrugations are shown as defined ribs and recesses representing a repeating unit, undulations and perturbations may be present on the repeating pattern as shown. Hence corrugations may not always be an exact repeating unit.

Particularly in the case of more distal tortuous anatomy, it may be required to achieve a lower bend radius distally than proximally. Similarly, more stiffness and pushability may be desirable proximally than distally.

The volume of jacket material across a length of the catheter may be altered locally to avoid an increase in corrugate height. In one configuration the volume of the jacket material is tailored such that the outer diameter of the catheter is maintained constant along a section of catheter, while the residual depth of the corrugations is reduced. The volume of the jacket may be reduced by reducing its thickness.

Reducing the thickness of the jacket also serves to reduce the residual depth following application of the cinch wire at a given tensions, further improving the flexibility of the catheter.

In another configuration, a lower volume of jacket material per unit length is used in a more distal region compared to a more proximal region to achieve a lower rib height distally than proximally. This allows for a lower outer diameter of the catheter distally than proximally, in tandem with a deeper corrugation. This further reduces the change of contact between adjacent corrugates during bending.

Figure 6:
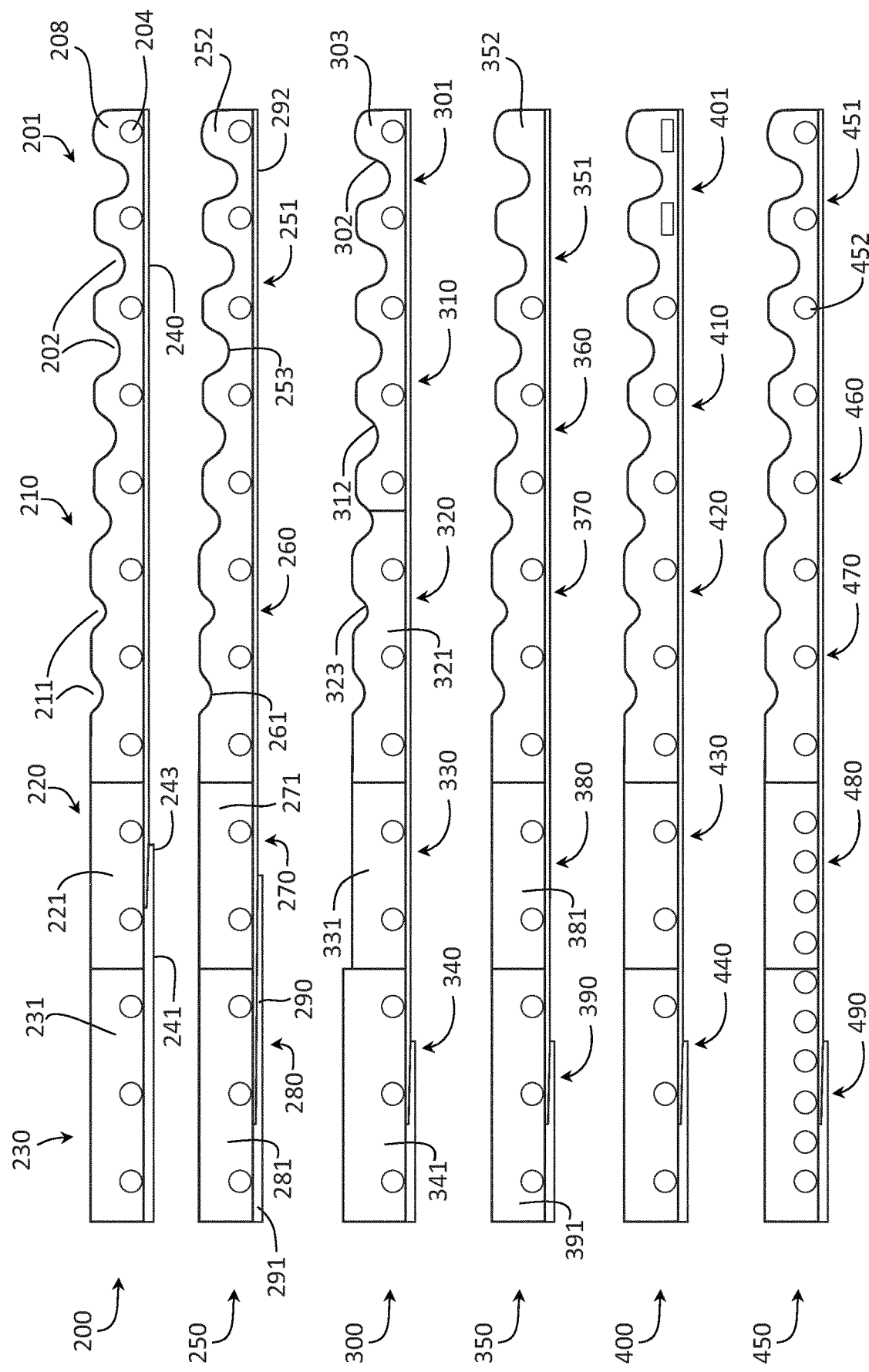
FIG. 6 shows part longitudinal sectional views of distal portions of six additional catheters.

Other arrangements are shown schematically in FIG. 6. In order from top to bottom:

Catheter 200: This has joint or overlap 243 of distal ePTFE liner 240 and proximal PTFE liner 241 within an un-corrugated portion 220. The proximal portion 220 has a jacket material 221 which is less flexible than the more distal jacket. Alternatively, 220 may represent an uncorrugated portion of the distal most jacket material. The joint 243 has a short overlap, such that there is a region of single layer of PTFE proximally, and ePTFE distally within that portion 220. Otherwise, this catheter 200 has portions from the distal end proximally:

First, or tip portion 201 with corrugations 202 in a jacket 203 and within which there is a helical support 204.

Second portion 210, with shallower corrugations 211.

Third portion 220, with un-corrugated jacket material 221, and surrounding the liner joint 243 between the ePTFE distal liner tube 240 and a proximal liner tube 241.

Fourth portion 230, with cylindrical un-corrugated jacket material 231.

Catheter 250 has a liner joint or overlap 290 of a distal ePTFE liner 291 and a proximal PTFE liner 291 which spans portions 270 and 280 with jacket materials 271 and 281 of different durometer. This has a first portion 251 with corrugations 253 in a jacket 252, a second portion 260 with shallower corrugations 261, a third portion 270 with un-corrugated jacket material 271, and a fourth portion 280 which is also un-corrugated. The liner joint 290 spans the portions 270 and 2280 with jackets of different hardness, the distal portion jacket 271 having greater flexibility In other examples, the lap joint may be located in any region or may span any two more regions of different jacket material.

Catheter 300 has a first portion 301 with a jacket material 303 of 80A hardness with corrugations 302, a second portion 310 with corrugations 312 of shallower depth, a third portion 320 with a different jacket material 321 and shallower corrugations 323, a fourth portion 330 of un-corrugated jacket material 331 of hardness 40D to 55D, and a fifth portion 340 with un-corrugated jacket material 341 of hardness 55D to 72D. In this case the lumen is formed by a distal liner of ePTFE which does not extend to the tip and which is joined in the fifth (proximal-most portion shown) to a PTFE proximal liner. In this embodiment any proximal jacket may be of a larger wall thickness than and more distal jacket such that it results in a stiffer portion of the catheter.

Catheter 350 has a first portion 351 with a jacket 352 without a helical support adjacent the tip. A second portion 360 has shallower or equal corrugations and the same jacket material 352. A third portion 370 with more shallow corrugations and the same jacket material 352. A fourth portion 380 has un-corrugated jacket material 381 which is stiffer or equal to the distal most jacket, and a fifth portion 390 has un-corrugated jacket material 391 of 40D to 55D or greater hardness. A liner joint is within the fifth portion 390. The first portion does not include a helical support.

In another embodiment the portion without a helical support may comprise un-corrugated jacket material such as un-corrugated 80A jacket material.

Catheter 400 has first, second, third, fourth, and fifth portions 401, 410, 420, 430, and 440. The first portion 401 does not include a helical support but has two marker bands or rings for radiopacity and to provide radial support.

Catheter 450 has first, second, third, fourth, and fifth portions 451, 460, 470, 480, and 490 respectively. In this case a helical support 452 has s smaller pitch in the more proximal portions.

Jackets of intermediate hardness to those described may be used, or by blending these durometers described above.

Where an increased hardness jacket is used next to a lower hardness jacket, an increase in the degree of corrugation locally may be used to avoid a sudden increase in stiffness.

These examples have some or all of the following attributes:
Reducing the wall thickness of the catheter wall or jacket in a more distal portion in order to manage flexibility.
Corrugation of more than one jacket.
Terminating the liner some distance proximal to the tip of the catheter.
Use of a corrugated area distally without a helical support.
Use of an uncorrugated area distally without a helical support.
Use of marker band for internal support at the distal tip (shown as rectangular cross section). These may be of a helical geometry of multiple pitches or are discrete circular rings of material.
Use of varying pitches of helical support, increasing periodically in increase stiffness.

Distal Tips

Figure 7:
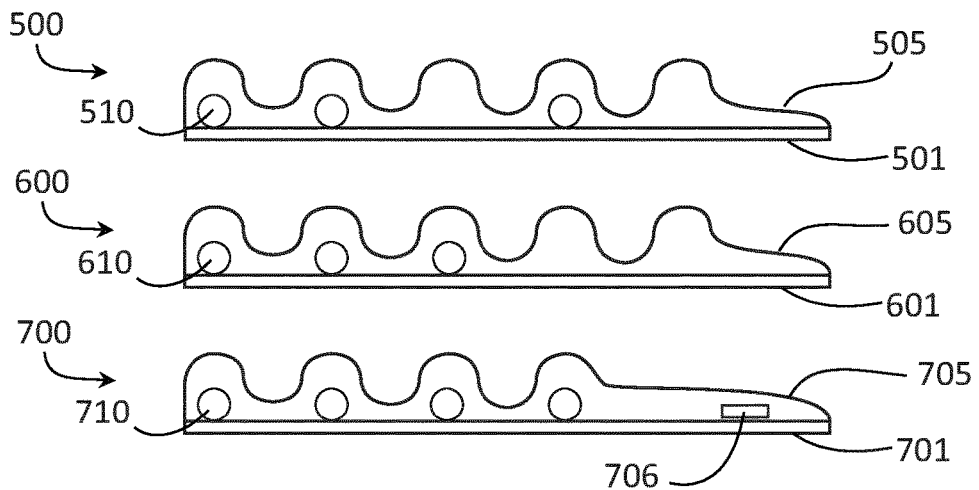
FIG. 7 shows distal tips of three additional catheters.

It may be preferable to have even more flexibility within the distal end of the catheter, such as the final 5 mm to 10 mm of the catheter. This is to ensure that the tip does not snag on the vessel wall and can track tortuous anatomy with or without the support of an internal catheter or wire. To achieve this, a number of approaches may be taken as outlined in FIG. 7.

In one example (500), the pitch of the helical support (510) is increased substantially such that one or more ribs of the corrugation are comprised of jacket material only, towards a tip 505. A liner 501 extends all of the way to the tip.

In another example (600) the helical support (610) is terminated such that one or more ribs of the corrugation in series comprise polymer only at the tip (605). Again, a liner 601 runs the full length to the tip.

In one configuration (700) a leading edge (705) of un-corrugated polymer without the presence of helical support (710) is used. A radiopaque marker band (706) may or may not be present in any of the above configurations. The region without a helical support may be corrugated or un-corrugated in any of the above configurations.

In at least some of these examples the first portion at the tip has a tapered outer surface, narrowing distally.

Dip Coating

In one method of manufacture, an ePTFE liner is placed on a mandrel. A helical support is placed on the liner. Dip coating is then used to apply a corrugated jacket, in which the coating takes the geometry of the liner and helical support. Multiple steps may be used to build up the jacket thickness such that the corrugations remain true and do not fill.

Liner Condition ePTFE is a material which by its fibrous and/or porous nature, can be stretched at least to some extent. During its manufacture, it can be difficult to control the wall thickness of the ePTFE liner.

Stretching may be performed in order to optimise the ePTFE liner for use in the catheter. This stretching can alter the directionality of the fibres and reduce the wall thickness as required. In one embodiment, the liner is radially stretched, by at least 10% in diameter.

When a catheter is in bending, there is a neutral axis, above which compression of the catheter wall is present, and below which tension is present.

To increase the force required to bend the catheter linear pre-stretching of the ePTFE on a mandrel may be performed. This removes "slack" or redundancy from the structure. Similarly shortening (to introduce slack) may be performed to reduce the force during bending. In one embodiment the liner is shortened by at least 10% in the distal region of the catheter tip in order to ensure a low force during bending.

In one method of manufacturing, etching is used to improve the potential to bond to the ePTFE liner, and to induce shortening. In one embodiment shortening of at least 10% is present in the ePTFE liner within 5 cm of the distal tip. More proximally the liner does not embody any shortening or is the liner is stretched.

A further characteristic of the fibrous liner is that it may be deformed beyond an elastic region. Beyond this elastic region the force required to further deform the liner is lower. Because of this, an ePTFE lined catheter may be "worked", or pre-conditioned using a series of bend and/or tension and/or compression cycles to enhance its flexibility.

In one embodiment, the catheter is pre-conditioned using bend and/or tension and/or compression cycles to enhance its flexibility.

Hybrid Device

The catheters described here achieve improved pushability arising from features such as corrugated urethane design with encapsulated helical support.

In one embodiment the distal end comprises distinct portions:

Proximal Encapsulated Portion: A corrugated section in which helical coil is embedded in a layer of urethane; the helical support being constrained from movement relative to the surrounding jacket material.

Distal ePTFE Floating portion: A corrugated section comprising an inner and outer layer of ePTFE with a helical support unbonded within helical channel The inner layer of ePTFE on the distal tip continues as a liner for the corrugated 80A section.

Figure 8A:
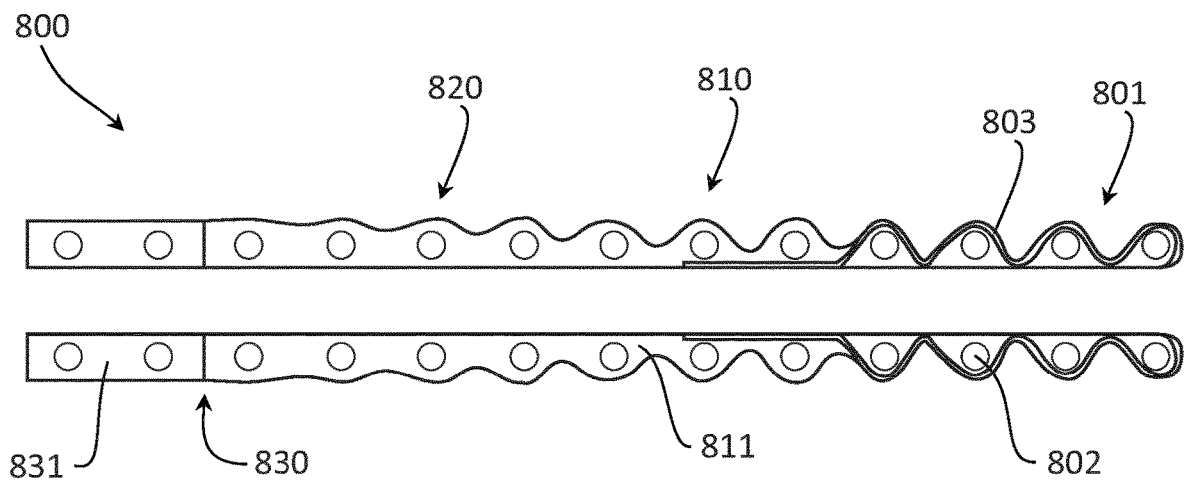
FIG. 8 shows a proximal encapsulated section and a distal floating coil section in a further catheter.

An example is shown in FIG. 8(a), which shows the distal end of a catheter 800, with a first portion 801, a second portion 810, a third portion 820, and a fourth portion 830 in the direction from distal to proximal. In the first portion 801 the coil 802 is floating, whereas in the second portion 810 it is embedded in jacket material 811.

Figure 8B:
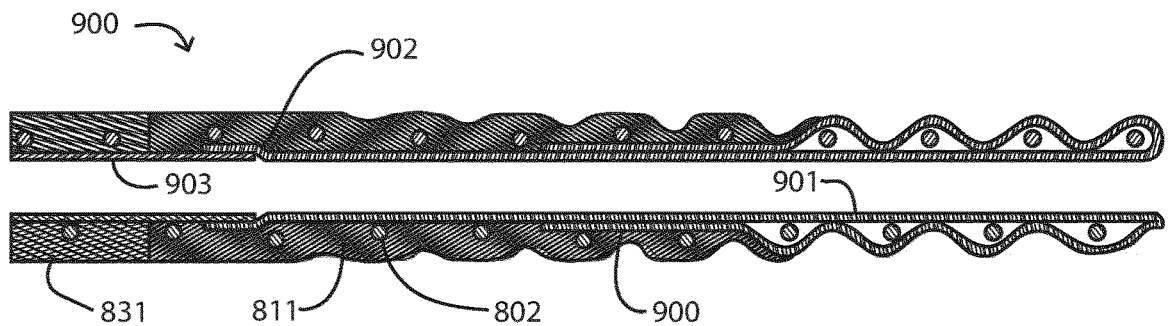

In FIG. 8(b) a configuration is shown in which the inner layer 901 of ePTFE on the distal tip continues as a liner for the corrugated 80A section. Further proximally the liner forms part of a lap joint 902 with a different liner 903 more proximally. In the configuration shown the inner layer of the distal tip overlaps itself as a double layer for a section before being a single layer within the 80A corrugated section.

In one example the distal floating arrangement has a length of at least 5 mm, preferably between 5 mm and 50 mm, more preferably between 5 mm and 20 mm.

Hydrophilic Coating

The catheter may have a hydrophilic coating over at least a portion. Hydrophilic coatings significantly reduce the amount of friction between the vessel wall and the catheter, allowing the catheter to be advanced or withdrawn without excessive effort. Furthermore, reduced friction means the transfer of displacement from the hub to the tip of the catheter is more efficient allowing more precise navigation by the physician.

Preferably the coating is applied across at least 20 cm of the length. Some coatings require the application of a primer layer typically comprised of a urethane, and an outer lubricous coating. The thickness of these layers should be minimised to avoid altering the stiffness of the tip. Any filling of the corrugation will reduce its effectiveness in achieving a flexible catheter section. In one configuration the coating layers are less than 0.002 in in thickness. Preferably the coating thickness is less than 0.001 in in thickness.

In one configuration the coating comprises a hydrogel which fills the corrugate. The hydrogel material has a stiffness much lower than that of the urethane jacket material of the catheter. Filling the corrugations will enable a smooth outer surface, or cushion, for contact with the vessel wall, while the hydrogel will provide lubricity without increasing the stiffness of the catheter section significantly. Such materials include but are not limited to poly(vinyl alcohol)-poly (acrylic acid) hydrogels.

Expandable Tip

In one configuration the distal tip of the catheter may expand or deform to enable it to accept a clot or embolus. That is to say, the most distal portion of the catheter is radially expandable such that during navigation to a target vessel it has a lower profile than when allowing a clot or other device to be pulled into the tip. This allows the tip to behave like an anaconda.

In one embodiment the tip of the catheter has a reduced radial stiffness compared to a region proximally, such that it can expand during entry of another body into its tip. In one embodiment the tip has a reducing wall thickness and or stiffness allowing greater radial expansion than a more proximal region.

In one embodiment the catheter is configured such that when a vacuum is applied pulling an embolus into the catheter tip, the most distal area expands, helping to engulf and deform the clot for entry into the proximal body of the catheter.

In one embodiment, the distal tip has a radial support preventing the tip from collapsing under vacuum, but allowing expansion upon entrance of a body larger than the diameter of the distal tip. The radial support in the tip may comprise a stent-like structure which can deform radially to enlarge and engulf the embolus.

In another configuration, the distal tip diameter tapers towards the end, but is expandable upon the application of a vacuum and entrance of an embolus into the catheter tip.

In another configuration, the radial support within the jacket at the distal tip comprises a ring which is not continuous and has a cut. This cut means that the radial support can open allowing the distal tip diameter to increase, but cannot reduce in diameter, preserving the lumen of the catheter during vacuum.

Coating

Figure 9A:
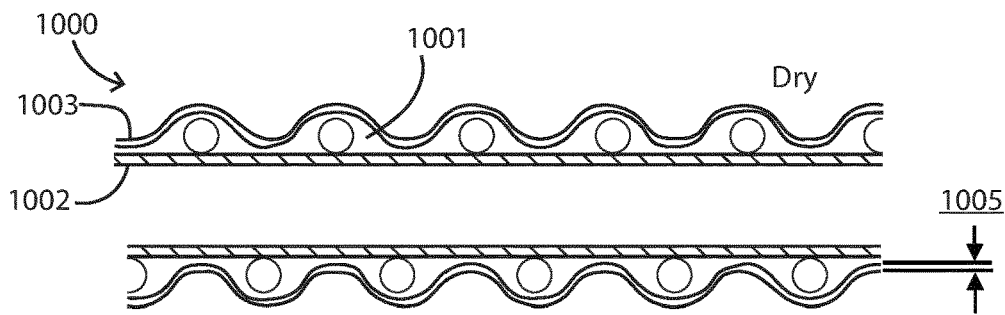
Figure 9B:
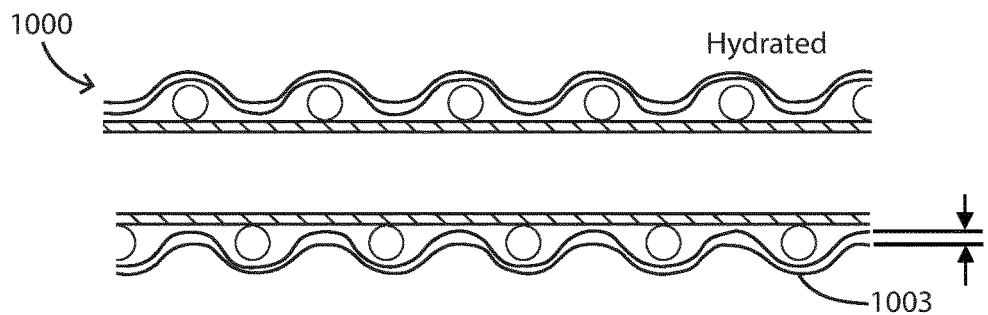

In general, following hydration, hydrophilic coatings swell and so take up a greater volume of space than when in the dry state as shown in FIGS. 9(a) and (b). In these drawings a portion of a catheter 1000 is shown, in which there is a jacket having a jacket body 1001 and a liner 1002 defining the lumen and an outer coating 1003. A helical support 1004 is within the jacket. The coating 1003 has a greater thickness 1005 when wet than dry. A greater degree of swelling may decrease the effective depth of the corrugations. This provides a smoother outer surface, with slightly less exaggerated corrugate geometry as shown in FIG. 9(b). This may be advantageous in navigation as it creates a smooth surface for interaction with the vessel wall.

An extreme example of this is shown in FIG. 10, for a catheter 1050 having a liner 1051, a jacket body 1052, a helical support 1054, and a hydrophilic coating 1053. The coating 1053 has swollen to fill the recess entirely, providing an un-corrugated outer surface.

For interfacial friction, increased area of contact increases the force required to overcome the friction. Accordingly, some corrugation pattern is preferable to reduce the area of contact while providing a relatively smooth interfacial surface.

In one example sufficient coating volume is present such that when hydrated the coating may swell outside the corrugate to some height above the top of the coated rib as shown in FIG. 11 for the catheter portion 1050. In this instance the coating creates a corrugation pattern atop the corrugation pattern of the base catheter, in which the jacket & coil define the corrugation pattern. The coating when hydrated creates a corrugation pattern which is the inverse of the corrugation pattern of the underlying jacket. In FIG. 11, the coating rib is 1058 and the recess is 1059. This is achieved by applying a sufficient volume of coating such that the height of the rib is lower than the adjacent height of the recess in the hydrated state. The following specifications apply in respect of the coating being hydrated, for example in water, saline, or blood. Specifically, hydrophilic coatings such as polyethely glycol, polyvinyl pyrrolidone or such derivatives may be used. Derivatives of phosphoryl choline, such as 2-methacryloxyethylphosphorylcholine in acrylic copolymers and water soluble polyvinylethers as well as hyaluronic acid may be also be tailored to achieve the following embodiments.

A benefit of a coating such as shown in FIG. 11 is that it the area of contact with the vessel is reduced thereby aiding navigation of the device.

Catheters described may be subject to extreme bending such that adjacent corrugations come closer together, or even into contact, reducing the space or volume within the recess as shown in FIG. 3. During this bending some of the coating may be compressed and squeezed out of the corrugation, becoming damaged or delaminating from the catheter wall and or coating matrix.

Coating Volume Minimization—Wet State

We describe coatings which swell in water to function as a hydrogel while remaining bound to the substrate (in this case the corrugated catheter wall). Poor adhesion or excessive deformation of the coating may cause it to shed, thus increasing the risk of embolism. During bending in navigation, the catheter is subject to tensile forces on the outside of the bend, and compressive forces on the inside of the bend as shown in FIGS. 12(a) and 12(b) in a catheter portion 1100. This has a concave (lower as illustrated) side and comprises a liner 1101 a jacket body 1102, a helical support 1103 and a coating 1104. FIG. 12(b) shows at 1108 coating deformation and at 1107 coating delamination. While the coatings remain intact on the tensile (top, convex) side of the bend, on the compressive side significant coating damage may be induced as adjacent corrugates can squeeze the coating between the ribs, eventually causing delamination.

Furthermore, adjacent corrugations coming into contact may increase the force required to cause bending and stiffening the catheter. To mitigate these issues the amount of coating within the corrugate may be minimized while maintaining sufficient lubricity, as shown in FIG. 12(a).

FIGS. 12(a) and (b) shows how, during bending, compression may deform and squeeze the coating. which may cause delamination of the coating from the rest of the coating itself or from the jacket substrate. The constituents of the coating may be tailored to adjust the degree of swelling which takes place when hydrated.

FIG. 12(c) shows at 1150 the volume of a recess and at 1155 the coating volume within the recess. In one example, the volume of coating is such that when in the hydrated state the ratio of hydrated coating volume within the recess to underlying recess volume per unit catheter length is less than 0.9, preferably less than 0.5, and more preferably less than 0.2, and even more preferably less than 0.1. In one configuration the thickness of the coating in the hydrated state is less than 0.05 mm, preferably less than 0.02 mm, more preferably less than 0.015 mm. In other examples, the coating has a thickness such that when hydrated its thickness at the bottom of the rib is less than 25% of the corrugate depth and or width, preferably less than 15% of the corrugate depth and or width, and even more preferably less than 10% of the corrugate depth and or width.

In other examples, the coating has a thickness such that when hydrated its thickness at the bottom of the rib is less than 20% of the height of the corrugate ($h_{cor}$), preferably less than 12% of the, and even more preferably less than 10%.

Coating Volume Minimization—Dry State

In one embodiment the thickness of the coating in the dry state is less than 0.010 mm, preferably less than 0.008 mm, more preferably less than 0.006 mm. In another embodiment, the dry thickness of the coating is less than 10% of the corrugate depth and or width. In another embodiment, the dry thickness of the coating is less than 3% of the corrugate depth and or width.

Selective Coating of Upper Section of Ribs

In general, the only portion of the corrugate which is in contact with the vessel wall is the upper section of the corrugate (the rib). The coating may be selectively applied to this area. This mitigates the potential for adjacent corrugates or areas of coating to come into contact during bending.

As shown in FIG. 13 in a catheter portion 1200 there is a liner 1201, a jacket body 1202, a helical support 1203, and a hydrophilic coating 1204 in a spiral pattern on the rib ridges. This is achieved by use of a masking element such as a wire 1205 shown in FIG. 14 to prevent application of the coating to the recess area of the corrugate. This leaves only the rib area exposed during application of the coating. In this example, the recess region of the corrugate is masked off using a wire or other means as shown in FIG. 14. The catheter is then coated by dipping, spray or other methods.

The coating may then be left to cure or dry. Subsequently the masking element is removed leaving coating behind on the convex portion of the corrugate only as shown in FIG. 13. Alternatively, the masking may be removed before the coating has dried.

Corrugate Size and Bending

In one embodiment, the volume of coating is limited such that in the hydrated state adjacent ribs do not come into contact during bending. In another embodiment adjacent corrugations may come into contact at a desired radius, but without any squeezing of the coating from within the corrugate.

In one embodiment, the jacket and coating are configured such that adjacent corrugates only contact one another at a certain the centre-line radius of curvature of the catheter in bending. FIG. 15 shows a catheter portion 1250 with segments 1251 and 1252 extending from a bend 1253 with a centre-line radius 1254 and an outer diameter 1255. In this case the radius 1254 is less than or equal to 2 times the diameter 1255 of the catheter, preferably less than or equal to 1 times the diameter of the catheter, and more preferably 0.7 times the outer diameter of the catheter.

In another embodiment, the coating and jacket are configured such that adjacent hydrated corrugates only contact one another when the centre-line radius of curvature of the catheter in bending is less than or equal to 2 times the diameter of the catheter, preferably at least 1 times the diameter of the catheter, and more preferably 0.7 times the outer diameter of the catheter.

Distal Tip and Proximal Shaft Joint

In some examples, the helical support in a distal portion of the catheter includes a super-elastic material such Nitinol, while the helical support in a more proximal portion includes a stiffer material such as stainless steel. This is to allow a flexible durable and kink resistant section distally and a stiffer section proximally to provide pushability and support.

In one example the catheter includes two portions as follows:
- a more distal portion with:
  - a liner,
  - an outer jacket being corrugated in at least one area,
  - a more proximal region which is less corrugated or un-corrugated, and
  - a helical support: and
- and a more proximal portion with:
  - a different liner to the one in the distal portion,
  - an outer jacket which is not corrugated, and
  - a helical support or braid which is stiffer than the support in the distal portion.

The distal and proximal regions of the catheter may be manufactured separately on individual mandrels and joined afterwards. Alternatively, they may be laid up on the one mandrel and reflowed to form a single unit. The more distal portion liner may be of primarily ePTFE, and the more proximal liner may be of primarily PTFE.

Alternatively, both the liner proximally and distally may be comprised of PTFE or ePTFE. This may be required in a situation in which two liners of the same material but of different thickness must be joined. Or in the case of ePTFE two different thicknesses and/or densities may be used proximally and distally.

Change in Type of Coil

The transition from a helical support of one type to another presents a challenge in terms of ensuring a stable joint, preventing kinking, and wire protrusion during manufacture and when the catheter is in use. Use of differing support wires (e.g. Nitinol and stainless steel) allows differing degrees of stiffness, dimensions, and ability to accommodate deformation elastically. A number of approaches are described here to ensure joint stability.

In one example it is preferable that the helical supports have the same direction of winding, both being right-handed or left-handed. This allows continuity of coil support, thereby reducing potential for stress concentrations.

The two types of helical support (or "coil") may be joined by a connecting element such as a weld. In one such configuration, the ends of the helical wires are joined end-on-end with a butt weld, while in another configuration they are bonded side-by side as shown in FIG. 16. In this catheter 1300 there is a first helical support 1301, a second helical support 1302 both on a jacket body 1304, and the supports being joined by a connecting element 1303. The connecting element 1303 is a hypo-tube crimped onto the ends of the wires 1301 and 1302 either side-by-side or end-on-end. The helical supports may be stabilized using a glue (such as Dymax™ UV cured adhesive or cyanacrylate).

It is advantageous to avoid sudden increase in stiffness in this region. In these situations, it is preferable to achieve increasing stiffness from distal to proximal regions. This allows transmission of force and displacement without buckling or kinking. Hence the embodiments described here and indicative stiffness associations are shown.

In one configuration the helical supports both being of the same direction of wind are wound within one another for at least one pitch as shown in FIG. 17, preferably for at least 2 pitches, more preferably at least 5 pitches, and even more preferably at least 10 pitches. This may be referred to as an interwoven configuration. In FIG. 17 a catheter 1400 has a liner 1401, a first helical support of relatively small wire diameter 1402, and a second helical support or relatively large wire diameter 1403 which are inter-woven in a region 1404. FIG. 17 also shows a plot representing change in stiffness along the catheter from the distal section (left) to the proximal section (right) for the configuration shown. The first helical support 1402 represents a distal region of the catheter, while the second helical support 1403 is in a more proximal region of the catheter, and the distal helical support being of flexible (e.g. of Nitinol) and the proximal support being stiffer (e.g. of stainless steel).

If the helical supports are at the same pitch in the interwoven region as in their more proximal and distal regions there will be an increase in catheter stiffness in this area due to the presence of excess material which reduces catheter flexibility. It can also cause a propensity for kinking at the areas at either end of the interwoven region where the stiffness abruptly drops. This may be mitigated by adjusting the pitch of one or both helical supports in the interwoven region. In this example, the pitch of the stiffer coil (second helical support 1403) is larger in the interwoven region (Pitch 3, 1412) than outside the interwoven region (Pitch 4, 1413). This region of larger pitch is wound partially or entirely within the less stiff helical support. The pitch of the more flexible coil (first helical support 1402) is larger in the interwoven region (Pitch 2, 1411) than outside the interwoven region (Pitch 1). This region of larger pitch is wound partially or entirely within the more stiff helical support. The pitch of both the first and second helical coil is larger in the interwoven region (Pitch 2 and Pitch 3, 1411, 1412) than their respective pitches in the distal and more proximal areas (Pitch 1 and Pitch 4, 1410, 1413). The associated change in catheter stiffness is shown in the plot of FIG. 17.

More preferably the pitch of each support in the interwoven region is 2× times the pitch of the support outside the interwoven region. Thereby, when both coils are interwoven the space between adjacent turns of the wire can be consistent across all three regions of the joint as shown in FIG. 17.

In one example, one or both helical supports are fixed in place using a low-profile heat shrink such as PET with a thickness of 0.2 mm or less, preferably 0.025 mm or less. This may be encapsulated using polymer jacket flowed over the area in subsequent manufacturing steps.

Improved pushability and torqueability of the catheter can be achieved by having a braid support over some or all of its length. In one configuration the proximal portion of the catheter has a braid support while the distal portion contains a helical wire. "Pushability" is defined as the ability to transmit force from the proximal end of the catheter to the distal end of the catheter. "Torquability" is defined as the ability to transmit a rotation and or rotational force (torque) from the proximal end of the catheter to the distal end of the catheter.

In one example the helical support in the distal section is a continuation or extension of one of the wires from the proximal braid, while the other wires of the proximal braid wires have been terminated at the start of a distal section.

In one configuration the pitch of the extension wire from the braid reduces at or near the point of termination of the other braid wires. In one embodiment the extension wire of the braid is of larger cross section than the other wires in the braid. In another embodiment the extension wire of the braid, and at least one other wire of the braid is of larger cross section than the other wires in the braid.

In one other configuration the right-handed coils within the braid are terminated at a point beyond which the left-handed coils of the braid continue distally.

In another configuration the extension wire from the proximal braid, representing a second helical support is continued to overlap into the distal section of the catheter, and changes to a different (first) helical support using one of the means outlined above and according to FIG. 17.

FIG. 18 shows a catheter 1425 with a first helical support 1426, a second helical support 1427, and a liner 1428. The jacket body is not shown. There are first, second, third, and fourth pitches 1429, 1430, 1431, and 1432. The second pitch 1430 is the pitch of the first support 1426 being longer than the pitch of this support when not overlapped. Likewise, the third pitch 1431 is the overlapped pitch of the second support 1427, again being longer than that of this support alone (1432).

Change in Type of Liner

As shown in FIG. 6, a lap-joint may be used at the transition from one liner to another, in this case liners of ePTFE and PTFE material. Preferably, the inner diameter of the ePTFE liner is in contact with the outer diameter the PTFE liner. In one configuration the PTFE liner has an outer strike layer to improve its bond to the ePTFE liner. The strike layer has a thickness of less than 0.025 mm, more preferably 0.005 mm to 0.010 mm.

In one configuration the inner diameter of the ePTFE liner is etched in the region at which it overlaps the PTFE liner with a strike layer 1458 on its outer diameter as shown in FIG. 19. A number of approaches may be used to apply the etch, including a sodium-based etching solution such as Fluoro-Etch™, or via a process such as plasma etching.

The strike layer applied to the PTFE may include a soft thermoplastic such as polyether block aimide (Pebax™) or nylon or other polymer materials. Softer durometer strike layers may be more suitable to flexible portions of the device. In one configuration the strike layer on the PTFE is the same material as the outer jacket to which it is bonded. Strike layers may be applied to the outer side of the PTFE, and/or to the inner side of the ePTFE, in the configuration where the ePTFE is on the outside.

The lap joint is an area at which the outer diameter of the catheter and stiffness increase due to the overlapping thickness of the ePTFE and PTFE. Accordingly, the length of this lap joint should be as short as possible to maintain a low profile and flexible catheter, but long enough to ensure a good bond between the two liners. In one configuration the length of this joint is between 1 and 5 mm, preferably between 10 and 20 mm for an 8F catheter. Preferably the lap joint is at least 1 diameter in length, more preferably at least 2 diameters in length.

Joint Location

The change in liner type from a first liner (Liner) 1 to a second liner (Liner 2) may take place at the same location as the change in the helical support type. That is to say, the change in helical support type is present close to or over the region of change in liner type. To prevent stress concentrations, it is preferable to avoid multiple joints or changes in material on top of one another.

In one configuration, the transition from Liner 1 (ePTFE) to Liner 2 (PTFE) takes place proximal to the transition via an interwoven region from a flexible helical support to a stiffer helical support. In a more preferable configuration, the transition from ePTFE to PTFE takes place distal to the transition from a flexible helical support to a stiffer helical support as shown in FIG. 19. This shows a catheter 1450 with a first liner 1451, a second liner 1452, a first helical support 1453, and a second helical support 1454. These form a lap joint 1455 and an interwoven region 1456. This diagram also shows a strike layer 1458, as described above.

In some examples, the first liner is of the same material as the second liner, but having a different thickness. For example, a distal PTFE liner (Liner 1) may be of a lower thickness for enhanced flexibility than the proximal PTFE liner (Liner 2). In another example the liner may be of a different density and/or thickness where both liners are of ePTFE.

In FIG. 19 the plot in the lower part of the figure shows a representative change in stiffness along the catheter from the distal section (left) to the proximal section (right) for the configuration shown.

In yet another embodiment, the switch from Liner 1 to Liner 2, and from a flexible helical support to a stiffer helical support takes place at the same location, but within a stiffer jacket material than is present more distally. This has the effect of limiting the deformation which can take place in the area thus limiting the stress and strain locally and protecting the joints.

In one embodiment the transition from ePTFE to PTFE liners takes place in a jacket stiffer than 80A polyurethane. Preferably the ePTFE to PTFE transition takes place in a jacket of at least higher stiffness than a more distal jacket, preferably Shore 35D, more preferably Shore 40D, even more preferably Shore 55D, and even more preferably Shore 72D.

In one embodiment, the change in helical support types and liner types takes place in a single jacket type as shown in FIG. 20. This shows a catheter 1475 with a single jacket body 1471, and liners and coils as shown in FIG. 19. This figure also shows a representative change in stiffness along the catheter from the distal section (left) to the proximal section (right) for the configuration.

In another example a change in liner type takes place in a jacket of lower stiffness, at least one pitch of both types of helical support also being present in the jacket of lower stiffness, with the majority of the interwoven region present in a stiffer more proximal jacket as shown in FIG. 21. These changes in stiffness may be achieved in a transition portion by varying the durometer of the jacket or altering the thickness. More specifically, FIG. 21 shows a catheter 1500 having a distal portion with a liner 1501 and a lap joint with a liner 1502. The lap joint is in the distal portion with a more flexible jacket body 1505 and a first, more flexible, helical support 1503. The proximal portion has a jacket body 1506 of stiffer material and a stiffer (less flexible) helical support 1504. The relatively stiff helical support 1504 extends into the distal portion jacket body 1505 in the transition portion. In other examples the coils may overlap only in the distal, or only in the proximal jacket body.

This arrangement avoids a sudden step up or down in stiffness. It is preferable to ensure that the joint from one liner type to another is greater than a minimum distance 1507 away from an adjacent jacket of different composition as shown in FIG. 21. In one embodiment the distance should be at least 0.2 cm, more preferably at least 0.5 cm, and even more preferably at least 1 cm.

In some examples the change from one helical support type to another takes place in a more proximal portion of the catheter which is stiffer than a more flexible portion distally. This provides a more stable matrix for the change in helical support stiffness. This more flexible portion distally may be achieved by use of one or more jackets of progressively increasing stiffness from distal to proximal as shown in FIG. 22, distal being on left. This may be termed a transition zone of the catheter. In more detail, FIG. 22 shows a catheter 1550 distal end with progressively more flexible portions in the distal direction from right to left. There is a jacket body 1551 within which is embedded a lap joint 1557 between two liners 1560 and 1561 and a joint between a proximal coil (helical support) 1558 and a more flexible coil 1559 with wire of smaller diameter. The joint between the coils may simply be the termination of one and start of the other, or they may be physically connected by a connection element as described above, or they may overlap also as described above. The jacket bodies are, in series in the distal direction (right to left) 1552, 1551, 1553, 1554, and 1555. There is a separation 1565 between the end of the body 1552 and the start of the distal liner 1561, and a separation 1566 between the end of the first liner 1560 and the start of the next distal jacket body 1553.

At least one of the more distal jackets may be corrugated for some or all its length. Preferably a more proximal area is not corrugated. Throughout this specification, where a more distal portion is shown un-corrugated, this is merely an example to illustrate another aspect such as a liner or coil joint, and it is to be understood that one or more distal portions are preferably corrugated. Reference is made to FIGS. 1 to 8 and the accompanying description for details of these aspects.

FIG. 22 also shows a representation of reduction in stiffness in the distal direction, which is advantageously smooth, without any sharp transitions.

In yet another configuration the joint is present in a region of the catheter which will not be subject to significant bending during use. Therefore, the joint is proximal to the region of the catheter which enters the greatest tortuosity or repeated loading. It is likely to be used in a vessel which is characterized by extreme twists and turns, loop and kinks. In one embodiment the catheter is configured for navigation to the tortuous anatomy of the neurovasculature such as the M1 segment of the middle cerebral artery or distal regions of the internal carotid artery (ICA). In this instance it is preferable to maintain the joint proximal to the petrous bend and more preferably in the proximal part of the ICA. In one embodiment, the joint location is at least 5 cm from the catheter distal end, preferably at least 25 cm from the catheter distal end.

Mother and Daughter Catheter Systems

Vacuum Transmission

Two or more catheters of different sizes above may be used in combination with one another in a mother and daughter configuration. For example, a 6F may be used within an 8F catheter having an inner diameter which accommodates a 6F catheter.

A tight fit between the mother and daughter catheter means that application of a vacuum to the proximal end of the mother catheter may not be transferred to the distal end of the mother catheter since the daughter catheter causes an effective seal between the catheters, preventing vacuum transmission from a port on the mother catheter.

In some examples the catheters are sized such that there is a gap between the OD of the daughter catheter and the ID of the mother catheter. This means that the physician may apply a vacuum to the distal end of the mother catheter with the daughter catheter in place. This is shown in FIG. 23, in which a catheter assembly 1650 has a mother catheter 1651 and a daughter catheter 1652. There is an annular gap 1653 between the catheters 1652 and 1651 and a vacuum source connected to the hub of the catheter 1654 can apply suction through this gap as illustrated by the arrow in FIG. 23. Either or both of the catheters may encompass a corrugated region.

Translating one catheter within another in highly tortuous regions can cause the catheters to bind to one another. Maintaining clearance between the ID of one mother catheter and the OD of the daughter catheter reduces the potential for this binding to occur.

In various examples the gap has a radial dimension of between 2% and 20% of the ID of the mother catheter, preferably at least 5%, more preferably at least 10%. For example, if the ID of the mother catheter is 2.25 mm (0.088 in), and the outer diameter of the daughter catheter is 2.03 mm (0.080 in), a gap of 0.2 mm (0.008 in) will be present between the catheters, representing a gap in diameter of 9%.

In some examples, a gap of at least one-half French size is present between the mother and daughter catheters. In another embodiment a gap of at least one French size is present.

In various examples both the mother and daughter catheters are corrugated at the distal ends. While the inner diameter of these portions of the catheter are generally smooth and cylindrical, during bending and manipulation some impression of the corrugations on the inner diameter of the mother catheter may be present. The corrugations of the inner diameter of the mother catheter and outer of the daughter catheter can interact and bind preventing catheter advancement or withdrawal. Such binding may be substantially prevented by the gap as described above.

Subtle corrugation may be induced during bending on the inner diameter of the catheters outlined. This is because the presence of corrugations means non-uniform distribution of energy and deformation within the catheter wall. The interaction of these corrugations which occur during bending on the ID of a mother catheter may impede movement of another corrugated catheter (daughter) within the mother catheter.

In various examples the pitch of the corrugations is different in the mother catheter to the daughter catheter, reducing potential for corrugations on the ID of the mother catheter and OD of the daughter catheter to nestle within one another, thus preventing bending. The direction of the wind of the corrugations may be different, further reducing potential of the corrugations to snag on one another.

Tension Applied to Cinch Wire to Create Corrugation

A cinch wire may be used to impart a corrugation pattern onto the OD of the catheter. Depending on the application of use varying tension may be applied to the wire along a length of the catheter to control the depth and or width of corrugation.

In particular the profiles may be used in the neurovasculature in conjunction with the embodiments outlined in the tables below. It should be noted that a longer flexible distal catheter section may be preferable on a smaller catheter (e.g. 5 Fr) as it is generally intended to go more distally than a larger catheter. For example, a 5 Fr may be required to go as far as the M3 segment of the middle cerebral artery while an 8 Fr catheter will only required to go as far as the M1 segment of the middle cerebral artery. Intuitively one may expect therefore that more pronounced corrugation should be maintained for a longer distance of the distal catheter length, necessitating a higher force for a longer distance of the distal catheter length. However, at lower diameters for equivalent materials a catheter will be more flexible than its larger brethren. Furthermore, using the embodiments outlined, specifically jackets of durometer 80A-90A with an ePTFE liner, a relatively flexible catheter construction is achieved. Thus, a shorter length of corrugation may be used for smaller catheter diameters while still achieving a suitably flexible and pushable construction.

Method of Use of Mother and Daughter Catheter

It is a limitation of smaller aspiration catheters that the clot cannot be ingested. The technique in these instances is to cork the clot of the end of the catheter upon application of a vacuum and then to drag the clot out of the body. A known consequence of this technique is fragmentation of the clot during dragging, causing distal emboli.

When there is a very small gap present between the mother and daughter catheter to allow transmission of vacuum, this may be insufficient to enable substantial flow and vacuum build-up in the lumen of the mother catheter distal tip. In one embodiment effective transmission of vacuum is achieved by application of the vacuum to the daughter catheter as shown in FIG. 24. Arrow A is the vacuum applied to the annular gap and arrow B is that applied to the daughter catheter 1652.

In one method of use the physician uses a daughter aspiration catheter to grab a clot from a distal region of the vasculature, FIG. 24(a). The clot is then brought proximally to the mother catheter tip, or just inside the catheter tip FIG. 24(b). At this point the physician may wish to switch off the vacuum to the daughter catheter, and withdraw the daughter catheter slightly, allowing the mother catheter vacuum to be applied across its entire cross section, maximizing the force holding the clot and the potential for clot ingestion.

The daughter catheter 1652 may be further withdrawn such that upon application of a vacuum to the proximal end of the daughter catheter, a vacuum is activated at the distal end of the mother catheter FIG. 24(c). The clot is then grabbed by the vacuum present at the tip of the mother catheter 1651, increasing the force of aspiration due to the increased lumen surface area.

Finally, due to the increased force of aspiration the clot is ingested into the mother catheter FIG. 24(d). This ability to ingest the clot and limit the distance over which it is dragged reduces the potential for distal emboli.

FIG. 25 is a diagram showing transitions between catheter portions in a direction from proximal (left) and distal (right) in one example catheter 1800 having some of the features illustrated in the other drawings.

This illustrates in one diagram a number of the advantageous features of catheters of the invention, and some of these features may be employed without others in any catheter encompassed by the invention. For example, there may be a lap joint portion akin to 1804 but within a jacket with corrugations, and/or not adjacent a portion with interwoven coils.

The regions are set out in Table 2:

| | | |
|---|---|---|
| 1801 | Hub | |
| 1802 | Proximal support (also referred to as radial support or helical support or coil) | |
| 1803 | Interwoven Supports | |
| 1804 | Liner Lap Joint between a proximal liner and a distal liner of more flexibility | |
| 1805 | End of jacket material body which has a greater depth or stiffness, with a small step-down in depth or stiffness to the next more distal portion. | |
| 1806 | Jacket body which is still un-corrugated but has less depth or stiffness than the of the portion 1805 and more proximally | |
| 1807 | Change to increase in coil pitch, reduction in jacket stiffness | |
| 1808 | Shallow corrugations and width | |
| 1809 | Increasing corrugation depth and width | |
| 1810 | Further increase in corrugation depth | |
| 1811 | Distal Support (also referred to as radial support or helical support) | |
| 1812 | Marker Band | |
| 1813 | Atrumatic Tip | |
| 1814 | Distal end of the distal liner | |

Table 2, features in order towards the distal tip of a catheter, such features being advantageous when combined as some or all of the features in this table.

Any or all of these features may be present in a daughter or a mother catheter.

Preferred Configurations and Dimensions of Corrugated Catheters

Preferred attributes and catheter dimensions are outlined for a range of catheter sizes are outlined in Table 3 to Table 8. The dimensions shown represent a catheter without a hydrophilic coating. A reference configuration and associated parameters are shown in FIG. 2.

In one embodiment there is a reduction in the pitch of the distal helical support (coil pitch) within the un-corrugated area of the most distal jacket just proximal to the start of a stiffer and more proximal jacket. This reduction in pitch serves limit the sudden change in stiffness due to the change in jacket material.

TABLE 3

Preferred attributes for catheters with a flexible corrugated tip for intravascular use.

| Attribute | Preferable | More Preferable |
|---|---|---|
| Variance in depth of corrugation | Variable along length (increasing distally) | Variable along length (increasing distally) |
| Variance in width of corrugation | Variable along length (increasing distally) | No variable |
| Recess Geometry | Round, U, V, Square | U |
| Rib Geometry | Avoid square profile | Rounded edge, or inverted U |
| Distal Liner Material | PTFE or expanded PTFE (Fibrous and compressible) | ePTFE |
| Distal Liner Condition on Mandrel Distal Section of Tip | Radially Stretched | Radially stretched, Axially Compressed |
| Distal Liner Condition on Mandrel Proximal Section of Tip | Radially Stretched | Radially Stretched, Axially Stretched |
| Proximal Liner Material | ePTFE or PTFE or HDPE or Polyamide | PTFE with Strike Layer |
| Proximal Liner Strike Layer | None or TPU or Polyether block amide | Polyether block amide 52D or 35D, more ideally aligned with jacket outside liner |
| Distal helical Support Material | Nitinol or stainless steel or cobalt chromium or nlyon, or PET or other polymer | Superelastic Nitinol |
| Proximal Support Material | Nitinol or stainless steel or cobalt chromium or nlyon, or PET or other polymer | Stainless steel |
| Location of Corrugated Section | Within 80A section | Within distal area of 80A section, proximal to marker band |
| Location of ePTFE and PTFE Joint | Proximal to 80A section | Within 72D or stiffest polymer jacket |
| Location of ePTFE and PTFE Joint if configuration contains different helical supports distally and proximally | Proximal to corrugated 80A section | Proximal to 80A Section, distal to transition from distal helical support to proximal helical support and within stiffest polymer jacket |

TABLE 3-continued

Preferred attributes for catheters with a flexible corrugated tip for intravascular use.

| Attribute | Preferable | More Preferable |
|---|---|---|
| Type of Joint of ePTFE and PTFE | Overlap or Butt | Overlap/Lap |
| Distal Jacket Material | TPU or Pebax | 90A or 80A TPU |
| Proximal Jacket Material | High Durometer Thermoplastic | Polyether Block Amide 55D to 75D |
| Cinch Wire Shape | Round, Square, or Angled | Round |

TABLE 4

Preferred Attributes for a 5F Corrugated Catheter

| 5F Corrugated Catheter Attribute | Symbol | Range Min | Range Max | Preferable Min | Preferable Max |
|---|---|---|---|---|---|
| Catheter Outer Diameter (mm) | OD | 1.44 | 1.70 | 1.61 | 1.70 |
| Catheter Inner Diameter (mm) | ID | 1.06 | 1.55 | 1.34 | 1.53 |
| Distal Corrugation Depth (mm) | $d_{corr\ distal}$ | 0.016 | 0.138 | 0.050 | 0.125 |
| Distal Residual Depth (mm) | $d_{res}$ | 0.016 | 0.094 | 0.031 | 0.063 |
| Distal Corrugation Width (mm) | W | 0.016 | 0.156 | 0.094 | 0.150 |
| Rib fillet radius (mm) | $r_{rib}$ | 0.008 | 0.156 | 0.031 | 0.094 |
| Length of Corrugated Section (cm) | $L_{cor}$ | 6 | 18 | 7 | 12 |
| Length of Proximal Uncorrugated Section of Distal Jacket Material (cm) | $L_{uncor}$ | 1 | 10 | 4 | 6 |
| Distal Liner Density (g/cm³) | — | 0.4 | 1.2 | 0.4 | 0.6 |
| Distal Liner Thickness pre-assembly (mm) | $t_{distal\ liner}$ | 0.015 | 0.102 | 0.016 | 0.048 |
| Distal Liner % Radial Stretch (%) | — | 5 | 25 | 18 | 24 |
| Proximal Liner ID (mm) | — | 1.12 | 1.63 | 1.40 | 1.61 |
| Proximal Liner wall thickness (mm) | $t_{proximal\ liner}$ | 0.013 | 0.050 | 0.013 | 0.019 |
| Atraumatic Tip Length (Uncoiled section 80A length distal to radiopaque marker band) (mm) | — | 0.31 | 1.25 | 0.63 | 0.78 |
| Distal Helical Support Diameter (mm) | $ID_{Support\ Distal}$ | 1.19 | 1.50 | 1.31 | 1.44 |
| Distal Support Wire Diameter (mm) | $D_{coil\ Distal}$ | 0.048 | 0.125 | 0.056 | 0.069 |
| Proximal Helical Support Diameter (mm) | $ID_{Support\ Proximal}$ | 1.19 | 1.50 | 1.31 | 1.44 |
| Proximal Helical Wire Diameter (mm) | $D_{coil\ Proximal}$ | 0.069 | 0.125 | 0.084 | 0.109 |
| Distance of ePTFE and PTFE Joint from transition from adjacent jacket of a different stiffness/diameter (mm) | — | 2 | 20 | 5 | 15 |
| Length of Lap Joint (mm) | — | 3.1 | 18.8 | 5.6 | 6.9 |
| Length of Radial Support Overlap (mm) | — | 0.2 | 12.5 | 5.6 | 6.9 |
| Number of interwoven pitches in radial support overlap | — | 1 | 28 | 12 | 14 |
| Corrugation Pitch (mm) Distal Support Pitch (mm) | Corrugation Pitch $_{Distal}$ | 0.06 | 0.47 | 0.25 | 0.31 |
| Proximal Support Pitch (mm) | Corrugation Pitch $_{Proximal}$ | 0.06 | 0.47 | 0.19 | 0.25 |
| Cinch Wire Diameter (mm) | — | 0.031 | 0.250 | 0.119 | 0.131 |
| Winding Tension Applied to Cinch Wire at Distal End (N) | — | 1 | 25 | 4 | 8 |
| Winding Tension Applied to Cinch Wire at Proximal End (N) | — | 0 | 25 | 0 | 1 |
| Distal Jacket ID Pre Lamination (mm) | — | 1.56 | 2.38 | 1.66 | 1.84 |
| Distal Jacket Wall thickness Pre-Lamination (mm) | — | 0.048 | 0.095 | 0.063 | 0.079 |
| Proximal Jacket ID Pre Lamination (mm) | — | 1.56 | 2.19 | 1.66 | 1.84 |
| Proximal Jacket Wall Thickness Pre-Lamination (mm) | — | 0.063 | 0.125 | 0.088 | 0.113 |
| Volume of Proximal Jacket Per Unit Catheter Length (mm²/F) | | 0.32 | 0.91 | 0.48 | 0.69 |
| Volume of Distal Jacket Per Unit Catheter Length (mm²/F) | | 0.24 | 0.74 | 0.34 | 0.48 |

TABLE 5

Preferred Attributes for a 6F Corrugated Catheter

| 6F Corrugated Catheter Attribute | Symbol | Range Min | Range Max | Preferable Min | Preferable Max |
|---|---|---|---|---|---|
| Catheter Outer Diameter (mm) | OD | 1.73 | 2.03 | 1.95 | 2.03 |
| Catheter Inner Diameter (mm) | ID | 1.65 | 1.90 | 1.72 | 1.85 |
| Distal Corrugation Depth (mm) | $d_{corr\ distal}$ | 0.019 | 0.165 | 0.060 | 0.15 |
| Distal Residual Depth (mm) | $d_{res}$ | 0.019 | 0.113 | 0.038 | 0.08 |
| Distal Corrugation Width (mm) | W | 0.019 | 0.188 | 0.113 | 0.18 |
| Rib fillet radius (mm) | $r_{rib}$ | 0.009 | 0.188 | 0.038 | 0.113 |
| Length of Corrugated Section (cm) | $L_{cor}$ | 5 | 17 | 7 | 12 |
| Length of Proximal Uncorrugated Section of Distal Jacket Material (cm) | $L_{uncor}$ | 1 | 10 | 4 | 6 |
| Distal Liner Density (g/cm³) | — | 0.4 | 1.2 | 0.4 | 0.6 |
| Distal Liner Thickness pre-assembly (mm) | $t_{distal\ liner}$ | 0.015 | 0.102 | 0.019 | 0.057 |
| Distal Liner % Radial Stretch (%) | — | 5 | 25 | 18 | 24 |
| Proximal Liner ID (mm) | — | 1.73 | 2.00 | 1.81 | 1.94 |
| Proximal Liner wall thickness (mm) | $t_{proximal\ liner}$ | 0.013 | 0.050 | 0.015 | 0.023 |
| Atraumatic Tip Length (Uncoiled section 80A length distal to radiopaque marker band) (mm) | — | 0.38 | 1.50 | 0.75 | 0.94 |
| Distal Helical Support Diameter (mm) | $ID_{Support\ Distal}$ | 1.43 | 1.80 | 1.58 | 1.73 |
| Distal Support Wire Diameter (mm) | $D_{coil\ Distal}$ | 0.057 | 0.150 | 0.068 | 0.083 |
| Proximal Helical Support Diameter (mm) | $ID_{Support\ Proximal}$ | 1.43 | 1.80 | 1.58 | 1.73 |
| Proximal Helical Wire Diameter (mm) | $D_{coil\ Proximal}$ | 0.083 | 0.150 | 0.101 | 0.131 |
| Distance of ePTFE and PTFE Joint from transition from adjacent jacket of a different stiffness/diameter (mm) | — | 2 | 20 | 5 | 15 |
| Length of Lap Joint (mm) | — | 3.8 | 22.5 | 6.8 | 8.3 |
| Length of Radial Support Overlap (mm) | — | 0.3 | 15.0 | 6.8 | 8.3 |
| Number of interwoven pitches in radial support overlap | — | 1 | 28 | 12 | 14 |
| Corrugation Pitch (mm) | Corrugation Pitch | 0.08 | 0.56 | 0.30 | 0.38 |
| Distal Support Pitch (mm) | Pitch $_{Distal}$ | | | | |
| Proximal Support Pitch (mm) | Corrugation Pitch $_{Proximal}$ | 0.08 | 0.56 | 0.23 | 0.30 |
| Cinch Wire Diameter (mm) | — | 0.038 | 0.300 | 0.143 | 0.158 |
| Winding Tension Applied to Cinch Wire at Distal End (N) | — | 1 | 25 | 6 | 10 |
| Winding Tension Applied to Cinch Wire at Proximal End (N) | — | 0 | 25 | 0 | 1 |
| Distal Jacket ID Pre Lamination (mm) | — | 1.88 | 2.85 | 1.99 | 2.21 |
| Distal Jacket Wall thickness Pre-Lamination (mm) | — | 0.057 | 0.114 | 0.076 | 0.095 |
| Proximal Jacket ID Pre Lamination (mm) | — | 1.88 | 2.63 | 1.99 | 2.21 |
| Proximal Jacket Wall Thickness Pre-Lamination (mm) | — | 0.075 | 0.150 | 0.105 | 0.135 |
| Volume of Proximal Jacket Per Unit Catheter Length (mm²/F) | | 0.46 | 1.31 | 0.69 | 1.00 |
| Volume of Distal Jacket Per Unit Catheter Length (mm²/F) | | 0.35 | 1.06 | 0.49 | 0.69 |

TABLE 6

Preferred Attributes for a 7F Corrugated Catheter

| 7F Corrugated Catheter Attribute | Symbol | Range Min | Range Max | Preferable Min | Preferable Max |
|---|---|---|---|---|---|
| Catheter Outer Diameter (mm) | OD | 2.01 | 2.36 | 2.28 | 2.36 |
| Catheter Inner Diameter (mm) | ID | 1.49 | 2.10 | 1.87 | 2.05 |
| Distal Corrugation Depth (mm) | $d_{corr\ distal}$ | 0.022 | 0.193 | 0.070 | 0.175 |
| Distal Residual Depth (mm) | $d_{res}$ | 0.022 | 0.131 | 0.044 | 0.088 |
| Distal Corrugation Width (mm) | W | 0.022 | 0.219 | 0.131 | 0.210 |
| Rib fillet radius (mm) | $r_{rib}$ | 0.011 | 0.219 | 0.044 | 0.131 |
| Length of Corrugated Section (cm) | $L_{cor}$ | 4 | 16 | 10 | 14 |
| Length of Proximal Uncorrugated Section of Distal Jacket Material (cm) | $L_{uncor}$ | 1 | 10 | 4 | 6 |
| Distal Liner Density (g/cm³) | — | 0.4 | 1.2 | 0.4 | 0.6 |
| Distal Liner Thickness pre-assembly (mm) | $t_{distal\ liner}$ | 0.015 | 0.102 | 0.022 | 0.067 |
| Distal Liner % Radial Stretch (%) | — | 5 | 25 | 18 | 24 |

TABLE 6-continued

Preferred Attributes for a 7F Corrugated Catheter

| 7F Corrugated Catheter Attribute | Symbol | Range Min | Range Max | Preferable Min | Preferable Max |
|---|---|---|---|---|---|
| Proximal Liner ID (mm) | — | 1.56 | 2.21 | 1.97 | 2.15 |
| Proximal Liner wall thickness (mm) | $t_{proximal\ liner}$ | 0.013 | 0.050 | 0.018 | 0.026 |
| Atraumatic Tip Length (Uncoiled section 80A length distal to radiopaque marker band) (mm) | — | 0.44 | 1.75 | 0.88 | 1.09 |
| Distal Helical Support Diameter (mm) | $ID_{Support\ Distal}$ | 1.66 | 2.10 | 1.84 | 2.01 |
| Distal Support Wire Diameter (mm) | $D_{coil\ Distal}$ | 0.067 | 0.175 | 0.079 | 0.096 |
| Proximal Helical Support Diameter (mm) | $ID_{Support\ Proximal}$ | 1.66 | 2.10 | 1.84 | 2.01 |
| Proximal Helical Wire Diameter (mm) | $D_{coil\ Proximal}$ | 0.096 | 0.175 | 0.118 | 0.153 |
| Distance of ePTFE and PTFE Joint from transition from adjacent jacket of a different stiffness/diameter (mm) | — | 2 | 20 | 5 | 15 |
| Length of Lap Joint (mm) | — | 4.4 | 26.3 | 7.9 | 9.6 |
| Length of Radial Support Overlap (mm) | — | 0.3 | 17.5 | 7.9 | 9.6 |
| Number of interwoven pitches in radial support overlap | — | 1 | 28 | 12 | 14 |
| Corrugation Pitch (mm) Distal Support Pitch (mm) | Corrugation Pitch $_{Distal}$ | 0.09 | 0.66 | 0.35 | 0.44 |
| Proximal Support Pitch (mm) | Corrugation Pitch $_{Proximal}$ | 0.09 | 0.66 | 0.26 | 0.35 |
| Cinch Wire Diameter (mm) | — | 0.044 | 0.350 | 0.166 | 0.184 |
| Winding Tension Applied to Cinch Wire at Distal End (N) | — | 1 | 25 | 8 | 12 |
| Winding Tension Applied to Cinch Wire at Proximal End (N) | — | 0 | 25 | 0 | 1 |
| Distal Jacket ID Pre Lamination (mm) | — | 2.19 | 3.33 | 2.32 | 2.58 |
| Distal Jacket Wall thickness Pre-Lamination (mm) | — | 0.067 | 0.133 | 0.088 | 0.111 |
| Proximal Jacket ID Pre Lamination (mm) | — | 2.19 | 3.06 | 2.32 | 2.58 |
| Proximal Jacket Wall Thickness Pre-Lamination (mm) | — | 0.088 | 0.175 | 0.123 | 0.158 |
| Volume of Proximal Jacket Per Unit Catheter Length (mm$^2$/F) | | 0.63 | 1.78 | 0.94 | 1.36 |
| Volume of Distal Jacket Per Unit Catheter Length (mm$^2$/F) | | 0.47 | 1.44 | 0.67 | 0.94 |

TABLE 7

Preferred Attributes for an 8F Corrugated Catheter

| 8F Corrugated Catheter Attribute | Symbol | Range Min | Range Max | Preferable Range Min | Preferable Range Max |
|---|---|---|---|---|---|
| Catheter Outer Diameter (mm) | OD | 2.30 | 2.70 | 2.60 | 2.70 |
| Catheter Inner Diameter (mm) | ID | 1.70 | 2.40 | 2.14 | 2.34 |
| Distal Corrugation Depth (mm) | $d_{corr\ distal}$ | 0.025 | 0.220 | 0.080 | 0.200 |
| Distal Residual Depth (mm) | $d_{res}$ | 0.025 | 0.150 | 0.050 | 0.100 |
| Distal Corrugation Width (mm) | W | 0.025 | 0.250 | 0.150 | 0.240 |
| Rib fillet radius (mm) | $r_{rib}$ | 0.012 | 0.250 | 0.050 | 0.150 |
| Length of Corrugated Section (cm) | $L_{cor}$ | 4 | 15 | 12 | 14 |
| Length of Proximal Uncorrugated Section of Distal Jacket Material (cm) | $L_{uncor}$ | 1 | 8 | 3 | 5 |
| Distal Liner Density (g/cm$^3$) | — | 0.4 | 1.2 | 0.4 | 0.6 |
| Distal Liner Thickness pre-assembly (mm) | $t_{distal\ liner}$ | 0.015 | 0.102 | 0.025 | 0.076 |
| Distal Liner % Radial Stretch (%) | — | 5 | 25 | 20 | 22 |
| Proximal Liner ID (mm) | — | 1.79 | 2.52 | 2.20 | 2.40 |
| Proximal Liner wall thickness (mm) | $t_{proximal\ liner}$ | 0.013 | 0.050 | 0.020 | 0.030 |
| Atraumatic Tip Length (Uncoiled section 80A length distal to radiopaque marker band) (mm) | — | 0.50 | 2.00 | 1.00 | 1.25 |

TABLE 7-continued

Preferred Attributes for an 8F Corrugated Catheter

| 8F Corrugated Catheter | | Range | | Preferable Range | |
|---|---|---|---|---|---|
| Attribute | Symbol | Min | Max | Min | Max |
| Distal Helical Support Diameter (mm) | $ID_{Support\ Distal}$ | 1.90 | 2.40 | 2.10 | 2.30 |
| Distal Support Wire Diameter (mm) | $D_{coil}$ Distal | 0.076 | 0.200 | 0.090 | 0.110 |
| Proximal Helical Support Diameter (mm) | $ID_{Support\ Proximal}$ | 1.90 | 2.40 | 2.10 | 2.30 |
| Proximal Helical Wire Diameter (mm) | $D_{coil\ Proximal}$ | 0.110 | 0.200 | 0.135 | 0.175 |
| Distance of ePTFE and PTFE Joint from transition from adjacent jacket of a different stiffness/diameter (mm) | — | 2 | 20 | 5 | 15 |
| Length of Lap Joint (mm) | — | 5.0 | 30.0 | 9.0 | 11.0 |
| Length of Radial Support Overlap (mm) | — | 0.4 | 20.0 | 9.0 | 11.0 |
| Number of interwoven pitches in radial support overlap | — | 1 | 28 | 12 | 14 |
| Corrugation Pitch (mm) Distal Support Pitch (mm) | Corrugation Pitch $_{Distal}$ | 0.10 | 0.75 | 0.40 | 0.50 |
| Proximal Support Pitch (mm) | Corrugation Pitch $_{Proximal}$ | 0.10 | 0.75 | 0.30 | 0.40 |
| Cinch Wire Diameter (mm) | — | 0.050 | 0.400 | 0.190 | 0.210 |
| Winding Tension Applied to Cinch Wire at Distal End (N) | — | 1 | 25 | 11 | 14 |
| Winding Tension Applied to Cinch Wire at Proximal End (N) | — | 0 | 25 | 0 | 1 |
| Distal Jacket ID Pre Lamination (mm) | — | 2.50 | 3.80 | 2.65 | 2.95 |
| Distal Jacket Wall thickness Pre-Lamination (mm) | — | 0.076 | 0.152 | 0.101 | 0.127 |
| Proximal Jacket ID Pre Lamination (mm) | — | 2.50 | 3.50 | 2.65 | 2.95 |
| Proximal Jacket Wall Thickness Pre-Lamination (mm) | — | 0.100 | 0.200 | 0.140 | 0.180 |
| Volume of Proximal Jacket Per Unit Catheter Length (mm²/F) | | 0.82 | 2.32 | 1.23 | 1.77 |
| Volume of Distal Jacket Per Unit Catheter Length (mm²/F) | | 0.62 | 1.89 | 0.87 | 1.23 |

TABLE 8

Preferred Attributes for a 9F Corrugated Catheter

| 9F Corrugated Catheter | | Range | | Preferable | |
|---|---|---|---|---|---|
| Attribute | Symbol | Min | Max | Min | Max |
| Catheter Outer Diameter (mm) | OD | 2.59 | 3.04 | 2.93 | 3.04 |
| Catheter Inner Diameter (mm) | ID | 1.91 | 2.72 | 2.41 | 2.71 |
| Distal Corrugation Depth (mm) | $d_{corr\ distal}$ | 0.028 | 0.248 | 0.090 | 0.225 |
| Distal Residual Depth (mm) | $d_{res}$ | 0.028 | 0.169 | 0.056 | 0.113 |
| Distal Corrugation Width (mm) | W | 0.028 | 0.281 | 0.169 | 0.270 |
| Rib fillet radius (mm) | $r_{rib}$ | 0.014 | 0.281 | 0.056 | 0.169 |
| Length of Corrugated Section (cm) | $L_{cor}$ | 8 | 17 | 10 | 16 |
| Length of Proximal Uncorrugated Section of Distal Jacket Material (cm) | $L_{uncor}$ | 1 | 10 | 4 | 6 |
| Distal Liner Density (g/cm³) | — | 0.4 | 1.2 | 0.4 | 0.6 |
| Distal Liner Thickness pre-assembly (mm) | $t_{distal\ liner}$ | 0.015 | 0.102 | 0.028 | 0.086 |
| Distal Liner % Radial Stretch (%) | — | 5 | 25 | 18 | 24 |
| Proximal Liner ID (mm) | — | 2.01 | 2.84 | 2.48 | 2.70 |
| Proximal Liner wall thickness (mm) | $t_{proximal\ liner}$ | 0.013 | 0.050 | 0.023 | 0.034 |
| Atraumatic Tip Length (Uncoiled section 80A length distal to radiopaque marker band) (mm) | — | 0.56 | 2.25 | 1.13 | 1.41 |
| Distal Helical Support Diameter (mm) | $ID_{support\ Distal}$ | 2.14 | 2.70 | 2.36 | 2.59 |
| Distal Support Wire Diameter (mm) | $D_{coil}$ Distal | 0.086 | 0.225 | 0.101 | 0.124 |
| Proximal Helical Support Diameter (mm) | $ID_{support\ Proximal}$ | 2.14 | 2.70 | 2.36 | 2.59 |
| Proximal Helical Wire Diameter (mm) | $D_{coil\ Proximal}$ | 0.124 | 0.225 | 0.152 | 0.197 |

TABLE 8-continued

Preferred Attributes for a 9F Corrugated Catheter

| 9F Corrugated Catheter | | Range | | Preferable | |
|---|---|---|---|---|---|
| Attribute | Symbol | Min | Max | Min | Max |
| Distance of ePTFE and PTFE Joint from transition from adjacent jacket of a different stiffness/diameter (mm) | — | 2 | 20 | 5 | 15 |
| Length of Lap Joint (mm) | — | 5.6 | 33.8 | 10.1 | 12.4 |
| Length of Radial Support Overlap (mm) | — | 0.4 | 22.5 | 10.1 | 12.4 |
| Number of interwoven pitches in radial support overlap | — | 1 | 28 | 12 | 14 |
| Corrugation Pitch (mm) Distal Support Pitch (mm) | Corrugation Pitch $_{Distal}$ | 0.11 | 0.84 | 0.45 | 0.56 |
| Proximal Support Pitch (mm) | Corrugation Pitch $_{Proximal}$ | 0.11 | 0.84 | 0.34 | 0.45 |
| Cinch Wire Diameter (mm) | — | 0.056 | 0.450 | 0.214 | 0.236 |
| Winding Tension Applied to Cinch Wire at Distal End (N) | — | 1 | 25 | 12 | 16 |
| Winding Tension Applied to Cinch Wire at Proximal End (N) | — | 0 | 25 | 0 | 1 |
| Distal Jacket ID Pre Lamination (mm) | — | 2.81 | 4.28 | 2.98 | 3.32 |
| Distal Jacket Wall thickness Pre-Lamination (mm) | — | 0.086 | 0.171 | 0.114 | 0.143 |
| Proximal Jacket ID Pre Lamination (mm) | — | 2.81 | 3.94 | 2.98 | 3.32 |
| Proximal Jacket Wall Thickness Pre-Lamination (mm) | — | 0.113 | 0.225 | 0.158 | 0.203 |
| Volume of Proximal Jacket Per Unit Catheter Length (mm$^2$/F) | | 1.03 | 2.94 | 1.55 | 2.24 |
| Volume of Distal Jacket Per Unit Catheter Length (mm$^2$/F) | | 0.78 | 2.39 | 1.10 | 1.55 |

TABLE 9

Preferred dimensions for a Corrugated Catheter, expressed as a proportion of the catheter outer diameter (normalised against French size).

| Corrugated Catheter | | Dimensions/French size | | | |
|---|---|---|---|---|---|
| | | Range | | Preferable | |
| Attribute | Symbol | Min | Max | Min | Max |
| Catheter Outer Diameter (mm/F) | OD | 0.288 | 0.338 | 0.325 | 0.338 |
| Catheter Inner Diameter (mm/F) | ID | 0.213 | 0.300 | 0.268 | 0.293 |
| Distal Corrugation Depth (mm/F) | $d_{corr\ distal}$ | 0.0031 | 0.0275 | 0.0100 | 0.0250 |
| Distal Residual Depth (mm/F) | $d_{res}$ | 0.0031 | 0.0188 | 0.0063 | 0.0125 |
| Distal Corrugation Width (mm/F) | W | 0.0031 | 0.0313 | 0.0188 | 0.0300 |
| Rib fillet radius( mm/F) | $r_{rib}$ | 0.0015 | 0.0313 | 0.0063 | 0.0188 |
| Distal Liner Density (g/cm$^3$) | — | 0.3 | 1.2 | 0.4 | 0.9 |
| Distal Liner Thickness pre-assembly (mm/F) | $t_{distal\ liner}$ | 0.0019 | 0.0128 | 0.0031 | 0.0095 |
| Proximal Liner ID (mm) | — | 0.2231 | 0.3150 | 0.2750 | 0.3000 |
| Proximal Liner wall thickness (mm/F) | $t_{proximal\ liner}$ | 0.0016 | 0.0063 | 0.0025 | 0.0038 |
| Atraumatic Tip Length (Uncoiled section 80A length distal to radio-paque marker band) (mm/F) | — | 0.063 | 0.250 | 0.125 | 0.156 |
| Distal Helical Support Diameter (mm/F) | $ID_{Support\ Distal}$ | 0.238 | 0.300 | 0.263 | 0.288 |
| Distal Support Wire Diameter (mm/F) | $D_{coil}$ Distal | 0.010 | 0.025 | 0.011 | 0.014 |
| Proximal Helical Support Diameter (mm/F) | $ID_{Support\ Proximal}$ | 0.24 | 0.30 | 0.26 | 0.29 |
| Proximal Helical Wire Diameter (mm/F) | $D_{coil\ Proximal}$ | 0.014 | 0.025 | 0.017 | 0.022 |

TABLE 9-continued

Preferred dimensions for a Corrugated Catheter, expressed as a proportion of the catheter outer diameter (normalised against French size).

| Corrugated Catheter Attribute | Symbol | Dimensions/French size | | | |
|---|---|---|---|---|---|
| | | Range | | Preferable | |
| | | Min | Max | Min | Max |
| Distance of ePTFE and PTFE Joint from transition from adjacent jacket of a different stiffness/diameter (mm) | — | 2 | 20 | 5 | 15 |
| Length of Lap Joint (mm/F) | — | 0.6 | 3.8 | 1.1 | 1.4 |
| Length of Interwoven Section of Helical Supports Overlap (mm/F) | — | 0.04 | 2.5 | 1.1 | 1.4 |
| Number of interwoven pitches in radial support overlap | — | 1 | 28 | 12 | 14 |
| Corrugation Distal Support Pitch (mm/F) | Corrugation Pitch$_{Distal}$ | 0.013 | 0.094 | 0.050 | 0.063 |
| Proximal Support Pitch (mm/F) | Corrugation Pitch$_{Proximal}$ | 0.013 | 0.094 | 0.038 | 0.050 |
| Cinch Wire Diameter (mm/F) | — | 0.006 | 0.050 | 0.024 | 0.026 |
| Distal Jacket ID Pre Lamination (mm/F) | — | 0.31 | 0.48 | 0.33 | 0.37 |
| Distal Jacket Wall thickness Pre-Lamination (mm) | 0.31 | 0.48 | 0.33 | 0.37 | 0.31 |
| Proximal Jacket ID Pre Lamination (mm) | 0.010 | 0.019 | 0.013 | 0.016 | 0.010 |
| Proximal Jacket Wall Thickness Pre-Lamination (mm) | 0.31 | 0.44 | 0.33 | 0.37 | 0.31 |
| Volume of Proximal Jacket Per Unit Catheter Length (mm$^2$/F) | — | 0.013 | 0.036 | 0.019 | 0.028 |
| Volume of Distal Jacket Per Unit Catheter Length (mm$^2$/F) | — | 0.010 | 0.029 | 0.014 | 0.019 |

The invention is not limited to the embodiments described but may be varied in construction and detail.

The invention claimed is:

1. A catheter comprising a jacket and defining a lumen, and extending distally towards a tip, the catheter comprising a helical support within the jacket for at least some of a length of the jacket,
wherein a distal end of the catheter has a plurality of portions of different configurations for different bending and/or pushability characteristics, said plurality of portions including at least one corrugated portion with a corrugated jacket,
characterized in that,
the catheter has a hydrophilic coating over at least one distal corrugated portion,
the hydrophilic coating is applied across at least 20 cm of a length of the catheter, and
a thickness of the hydrophilic coating in a hydrated state is less than 25% of a corrugate depth.

2. The catheter as claimed in claim 1, where the lumen is provided by at least two liners joined at a joint, the joint is in a portion with an un-corrugated jacket, and the joint is at least 5 cm from the tip of the catheter.

3. The catheter as claimed in claim 1, wherein the hydrophilic coating has a primer layer of material.

4. The catheter as claimed in claim 3, wherein a thickness of the primer layer or primer layers is less than 0.051 mm (0.002 in).

5. The catheter as claimed in claim 1, wherein the hydrophilic coating comprises a hydrogel which fills at least part of a corrugate, and wherein the hydrogel has a stiffness lower than that of a material of the corrugated jacket.

6. The catheter as claimed in claim 1, wherein the thickness of the hydrophilic coating in the hydrated state is less than 0.05 mm.

7. The catheter as claimed in claim 1, wherein the thickness of the hydrophilic coating in the hydrated state at a bottom of a recess in a jacket corrugation is less than 20% of a height of a corrugate.

8. The catheter as claimed in claim 7, wherein a volume of the hydrophilic coating is such that, when in the hydrated state, a ratio of the volume of the hydrophilic coating within the recess of a corrugate to underlying recess volume per unit catheter length is less than 0.09.

9. The catheter as claimed in claim 1, wherein a dry thickness of the hydrophilic coating is less than 10% of the corrugate depth and/or a corrugate width.

10. The catheter as claimed in claim 1, wherein the jacket in a distal portion at least is configured such that, at least when dry, ribs only contact one another when a centre-line radius of curvature of the catheter is in bending.

11. The catheter as claimed in claim 10, wherein the centre-line radius of curvature of the catheter is less than or equal to 2 times a diameter of the catheter.

12. The catheter as claimed in claim 11, wherein the hydrophilic coating is configured such that adjacent hydrated corrugates only contact one another when the centre-line radius of curvature of the catheter in bending is less than or equal to 2 times of the diameter of the catheter.

13. The catheter as claimed in claim 1, wherein the catheter comprises a plurality of helical supports, and wherein a first helical support in a more distal portion of the catheter is more flexible than a second helical support in a more proximal portion of the catheter, and wherein the plurality of helical supports are different and overlap, and wherein the catheter comprises a proximal liner and a distal liner joined at a lap joint, and optionally a number of helical support turns which overlap in an interwoven region is in a range of 3 to 12.

14. The catheter as claimed in claim 13, wherein the lap joint is at least 5 cm from the tip of the catheter, a more distal portion liner comprises primarily expanded polytetrafluoroethylene (ePTFE), and a more proximal portion liner comprises PTFE.

15. The catheter as claimed in claim 1, wherein the catheter comprises a plurality of helical supports, and wherein a first helical support in a more distal portion of the catheter is more flexible than a second helical support in a more proximal portion of the catheter, wherein the plurality of helical supports have a same winding direction, wherein the plurality of helical supports are wound within one another for at least 5 pitches, and wherein at least one helical support has a larger pitch in an inter-woven region than in other catheter portions in which the plurality of helical supports are not interwoven.

* * * * *